US009995739B2

United States Patent
Dunaway

(10) Patent No.: US 9,995,739 B2
(45) Date of Patent: Jun. 12, 2018

(54) PROTEIN DETECTION VIA NANOREPORTERS

(71) Applicant: NanoString Technologies, Inc., Seattle, WA (US)

(72) Inventor: Dwayne L. Dunaway, Seattle, WA (US)

(73) Assignee: NanoString Technologies, Inc., Seattle, WA (US)

( * ) Notice: Subject to any disclaimer, the term of this patent is extended or adjusted under 35 U.S.C. 154(b) by 77 days.

(21) Appl. No.: 14/814,216

(22) Filed: Jul. 30, 2015

(65) Prior Publication Data

US 2016/0003809 A1   Jan. 7, 2016

Related U.S. Application Data

(63) Continuation of application No. 12/904,078, filed on Oct. 13, 2010.

(60) Provisional application No. 61/251,192, filed on Oct. 13, 2009, provisional application No. 61/325,224, filed on Apr. 16, 2010, provisional application No. 61/326,787, filed on Apr. 22, 2010.

(51) Int. Cl.
*G01N 33/68* (2006.01)
*G01N 33/53* (2006.01)

(52) U.S. Cl.
CPC ..... *G01N 33/5306* (2013.01); *G01N 33/6803* (2013.01); *C12Q 2537/125* (2013.01); *G01N 2333/55* (2013.01); *G01N 2458/10* (2013.01)

(58) Field of Classification Search
CPC .......... G01N 33/5306; G01N 33/6803; G01N 2333/55; G01N 2458/10; C12Q 2537/125
See application file for complete search history.

(56) References Cited

U.S. PATENT DOCUMENTS

| | | |
|---|---|---|
| 5,185,243 A | 2/1993 | Ullman et al. |
| 5,320,814 A | 6/1994 | Walt et al. |
| 5,543,838 A | 8/1996 | Hosier et al. |
| 5,831,012 A | 11/1998 | Nilsson et al. |
| 6,207,392 B1 | 3/2001 | Weiss et al. |
| 6,268,147 B1 | 7/2001 | Beattie et al. |
| 6,429,027 B1 | 8/2002 | Chee et al. |
| 6,544,738 B2 | 4/2003 | Wold |
| 6,602,661 B1 | 8/2003 | Knezevic et al. |
| 6,635,452 B1 | 10/2003 | Monforte et al. |
| 6,596,257 B2 | 11/2003 | Bryan |
| 6,690,470 B1 | 2/2004 | Baer et al. |

(Continued)

FOREIGN PATENT DOCUMENTS

| | | |
|---|---|---|
| EP | 320308 A2 | 6/1989 |
| EP | 439182 A2 | 7/1991 |

(Continued)

OTHER PUBLICATIONS

Alfano et al., "Optical Sensing, Imaging, and Manipulation for Biological and biomedical applications" SPIE—The International Society for Optical Engineering, Jul. 2000, vol. 4082, Taiwan.

(Continued)

*Primary Examiner* — Jeremy C Flinders
(74) *Attorney, Agent, or Firm* — Cooley LLP; Ivor R. Elrifi; Matthew Pavao

(57) ABSTRACT

The invention provides methods, compositions, kits and devices for the detection of proteins. In some embodiments, the invention allows for multiplexed protein detection.

17 Claims, 16 Drawing Sheets
(14 of 16 Drawing Sheet(s) Filed in Color)

(56) References Cited

U.S. PATENT DOCUMENTS

| | | |
|---|---|---|
| 6,942,968 B1 | 9/2005 | Dickinson et al. |
| 7,060,507 B2 | 6/2006 | Akeson et al. |
| 7,132,519 B2 | 11/2006 | Monforte et al. |
| 7,214,477 B1 | 5/2007 | Emmert-Buck |
| 7,402,398 B2 | 7/2008 | Pidaparthi et al. |
| 7,402,399 B2 | 7/2008 | Mukherjeei et al. |
| 7,473,767 B2 | 1/2009 | Dimitrov |
| 7,553,619 B2 | 6/2009 | Kumar et al. |
| 7,569,392 B2 | 8/2009 | Levy et al. |
| 7,588,906 B2 | 9/2009 | Brueggemeier et al. |
| 7,648,828 B2 | 1/2010 | Chan-Hui et al. |
| 7,728,287 B2 | 6/2010 | Felton et al. |
| 7,786,352 B2 | 8/2010 | Moloney et al. |
| 8,003,312 B2 | 8/2011 | Krutzik et al. |
| 8,206,901 B2 | 6/2012 | Freskgard et al. |
| 8,221,972 B2 | 7/2012 | LeMaire et al. |
| 8,247,180 B2 | 8/2012 | Pidaparthi et al. |
| 8,309,306 B2 | 11/2012 | Nolan et al. |
| 8,349,574 B2 | 1/2013 | Bates et al. |
| 8,362,415 B2 | 1/2013 | Felton et al. |
| 8,486,623 B2 | 7/2013 | Monforte et al. |
| 8,637,650 B2 | 1/2014 | Cherasov et al. |
| 8,653,242 B2 | 2/2014 | Neville |
| 8,753,824 B2 | 6/2014 | Papin et al. |
| 8,822,158 B2 | 9/2014 | Froehlick et al. |
| 8,865,414 B2 | 10/2014 | Hennig et al. |
| 8,906,700 B2 | 12/2014 | Lim et al. |
| 9,046,477 B2 | 6/2015 | Emedcoles et al. |
| 9,228,948 B2 | 1/2016 | Emedcoles et al. |
| 9,297,762 B2 | 3/2016 | Emedcoles et al. |
| 9,304,084 B2 | 4/2016 | Emedcoles et al. |
| 2001/0002315 A1 | 5/2001 | Schultz et al. |
| 2001/0007775 A1 | 7/2001 | Seul et al. |
| 2001/0023078 A1 | 9/2001 | Bawendi et al. |
| 2001/0029049 A1 | 10/2001 | Walt et al. |
| 2001/0034034 A1 | 10/2001 | Bruchez et al. |
| 2001/0053334 A1 | 12/2001 | Chen et al. |
| 2002/0028457 A1 | 3/2002 | Empedocles et al. |
| 2002/0034737 A1 | 3/2002 | Drmanac |
| 2002/0034827 A1 | 3/2002 | Singh et al. |
| 2002/0039728 A1 | 4/2002 | Kain et al. |
| 2002/0051971 A1 | 5/2002 | Stuelpnagel et al. |
| 2002/0068018 A1 | 6/2002 | Pepper et al. |
| 2002/0177141 A1 | 11/2002 | Chee et al. |
| 2002/0187515 A1 | 12/2002 | Chee et al. |
| 2003/0008323 A1 | 1/2003 | Ravkin et al. |
| 2003/0013091 A1 | 1/2003 | Dimitrov |
| 2003/0028981 A1 | 2/2003 | Chandler et al. |
| 2003/0186426 A1 | 10/2003 | Brewer et al. |
| 2005/0037397 A1 | 2/2005 | Mirkin et al. |
| 2005/0048498 A1 | 3/2005 | Woudenberg et al. |
| 2005/0233318 A1 | 10/2005 | Chee et al. |
| 2007/0166708 A1 | 7/2007 | Dimitrov et al. |
| 2009/0220978 A1 | 9/2009 | Dimitrov |
| 2010/0047924 A1 | 2/2010 | Webster et al. |
| 2010/0261026 A1 | 10/2010 | Ferree et al. |
| 2011/0086774 A1 | 4/2011 | Dunaway |
| 2011/0223613 A1 | 9/2011 | Gut |

FOREIGN PATENT DOCUMENTS

| | | |
|---|---|---|
| EP | 0963443 B1 | 6/1998 |
| WO | WO-1990/001069 A1 | 2/1990 |
| WO | WO-9707245 | 2/1997 |
| WO | WO-9714028 | 4/1997 |
| WO | WO-9918434 | 4/1999 |
| WO | WO-200073777 | 12/2000 |
| WO | WO-200100875 | 1/2001 |
| WO | WO-2001/057268 A2 | 8/2001 |
| WO | WO-2003/003810 A2 | 1/2003 |
| WO | WO-2005/003394 A2 | 1/2005 |
| WO | WO-2005/071401 A2 | 8/2005 |
| WO | WO-2007/076128 A2 | 7/2007 |
| WO | WO-2007/076132 A2 | 7/2007 |
| WO | WO-2007/112012 A2 | 10/2007 |
| WO | WO 2008/122310 A1 | 10/2008 |
| WO | WO-2008/124847 A2 | 10/2008 |
| WO | WO-2010/019826 A1 | 2/2010 |

OTHER PUBLICATIONS

Ferguson et al., "High-Density Fiber-Optic DNA Random Microsphere Array" *Analytical Chemistry* 72 (22), 5618-5624 (2000).

Steemers et al., "Screening unlabeled DNA targets with randomly ordered fiber-optic gene arrays." *Nature Biotechnology.* 18, 91-94 (2000).

Werner et al., "Current status of DNA sequencing by single molecule detection" Proc. SPIE 3602, Advances in Fluorescence Sensing Technology IV, 355, (1999).

Blank et al., "Double-chip protection arrays: force-based multiplex sandwich immunoassays with increased specificity", *Anal. Bioanal. Chem.*, 379(7-8):974-981 (2004).

Boozer et al., "DNA directed protein immobilization on mixed ssDNA/oligo(ethylene glycol) self-assembled monolayers for sensitive biosensors", *Analytical Chemistry*, 76(23):6967-6972 (2004).

Gold, "Oligonucleotides as research, diagnostic, and therapeutic agents", *J. Biol. Chem.*, 270(23):13581-13584 (1995).

Gullberg et al., "Cytokine detection by antibody-based proximity ligation", *PNAS*, 101(22):8420-8424 (2004).

Hans et al., "Protein-mediated sandwich strategy for surface-enhanced Raman scattering: application to versatile protein detection", *Anal. Chem.*, 81(9):3350-3355 (2009).

Jayasena, "Aptamers: an emerging class of molecules that rival antibodies in diagnostics", *Clin. Chem.*, 45:1628-1650 (1999).

Jermutus et al., "Ligand binding of a ribosome-displayed protein detected in solution at the single molecule level by fluorescence correlation spectroscopy", *Eur. Biophys. J.*, 31:179-184 (2002).

Kang et al., "Electrochemical detection of thrombin by sandwich approach using antibody and aptamer", *Bioeletrochem.*, 73:76-81 (2008).

Kozlov et al., "Efficient strategies for the conjugation of oligonucleotides to antibodies enabling highly sensitive protein detection", *Biopolymers*, 73(5):621-630 (2004).

Maynard et al., "Antibody Engineering", *Ann. Rev. Biomed. Eng.*, 2:339-376 (2000).

Nolan, "Tadpoles by the tail", *Nature Methods*, 2:11-12 (2005).

Sasajima et al., "Detection of protein tyrosine phosphorylation by open sandwich fluoroimmunoassay", *Biotechnol. Prog.*, 22(4):968-973 (2006).

Sieber et al., "Selecting proteins with improved stability by a phage-based method", *Nat. Biotechnol.*, 16(10):955-960 (1998).

Simon et al., "Peptoids: a modular approach to drug discovery", *PNAS*, 89(20):9367-9371 (1992).

Spada et al., "Selectively infective phages (SIP)", *Biol. Chem.*, 378:445-456 (1997).

Stoeva et al., "Mltiplexed Detection of Protein Cancer Markers with Biobarcoded Nanoparticle Probes." *J. Amer. Chem. Soc* 128:8378-8379 (2006).

Wilson et al., "In vitro selection of functional nucleic acids", *Ann. Rev. Biochem.*, 68:611-647 (1999).

Wlotzka et al., "In vivo properties of an anti-GnRH Spiegelmer: an example of an oligonucleotide-based therapeutic substance class", *PNAS*, 99:8898-8902 (2002).

Sacca, F. et al., "A Combined Nucleic Acid and Protein Analysis in Friedreich Ataxia: Implications for Diagnosis, Pathogenesis and Clinical Trial Design," *PLoS ONE*, vol. 6, No. 3, Mar. 11, 2011, e17627, 9 pages.

Mao, X. et al., "Simultaneous Detection of Nucleic Acid and Protein Using Gold Nanoparticles and Lateral Flow Device," *Anal Sci.*, vol. 30, No. 6, Jan. 1, 2014, pp. 637-642.

5) Bridging oligo has a purification tag (sequence or biotin).

6) Release oligo (via disulfide reduction, uracil excision, restriction digest, or proteinase K, etc.)

7) Purify signal oligo via tag (sequence or biotin). Only the ligated oligo will have enough overlap to remain hybridized to signal oligo.

8) Run through normal nCounter assay.

FIGURE 9

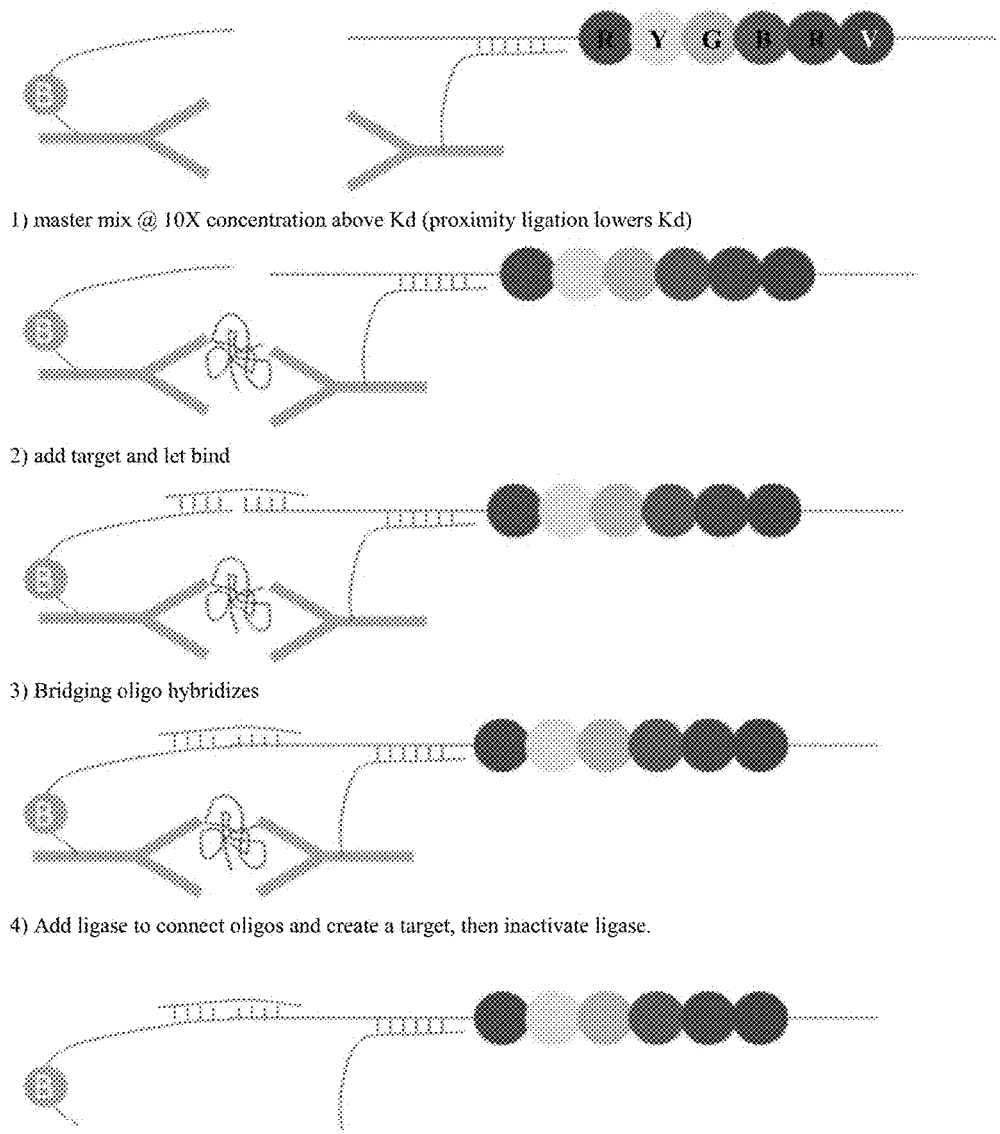

1) master mix @ 10X concentration above Kd (proximity ligation lowers Kd)

2) add target and let bind

3) Bridging oligo hybridizes

4) Add ligase to connect oligos and create a target, then inactivate ligase.

5) Release oligo (via disulfide reduction, uracil excision, restriction digest, or proteinase K, etc.). Note: this step may not be needed.
6) run through normal protocol on Prep Station and read on Digital analyzer. There is no hybridization to reporters.

PROTEIN DETECTION VIA NANOREPORTERS

RELATED APPLICATIONS

This application is a continuation of U.S. Ser. No. 12/904,078, filed Oct. 13, 2010. U.S. Ser. No. 12/904,078 claims the benefit of provisional applications U.S. Ser. No. 61/251,192, filed Oct. 13, 2009; U.S. Ser. No. 61/325,224, filed Apr. 16, 2010; and U.S. Ser. No. 61/326,787, filed Apr. 22, 2010. The contents of the aforementioned applications are each herein incorporated by reference in their entireties.

FIELD OF THE INVENTION

The present invention relates generally to field of protein detection, quantification, identification, and multiplex analysis using the tools of molecular biology to generate unique nanoreporter constructs and the methods for using them.

BACKGROUND OF THE INVENTION

With the recent completion of analysis of the human genome, much attention is now shifting to the field of proteomics, where gene products (proteins), their variants, interacting partners and the dynamics of their regulation and processing are the emphasis of study. Such studies are essential in understanding, for example, the mechanisms behind genetic/and environmentally induced disorders or the influences of drug mediated therapies, as well as potentially becoming the underlying foundation for further clinical and diagnostic analyses. Critical to these studies is the ability to qualitatively determine specific variants of whole proteins (e.g., splice variants, point mutations, post-translationally modified versions, and environmentally/therapeutically-induced modifications) and the ability to view their quantitative modulation. Moreover, it is becoming increasingly important to perform these analyses from not just one, but multiple biological fluids/extracts. There are limited methods of multiplexed protein measurement technologies due to the additional challenges inherent in protein samples.

However, measurement of proteins in biological fluid is difficult due to their inherent properties. Accordingly, there is a pressing need for rapid, sensitive, reproducible, and accurate analytical approaches for the analysis of proteins and their variants.

In order to analyze proteins of interest from—and in—their native environment, assays capable of assessing proteins present in a variety of biological fluids and/or extracts, both qualitatively and quantitatively, are needed.

SUMMARY OF THE INVENTION

The invention provides method and compositions for analysis of proteins. In some embodiments, the invention provides methods and compositions for the detection and/or quantification of proteins in a sample. In some embodiments, the invention provides methods determining the concentration of at least one protein in a sample comprising the steps of: (a) providing: (i) at least one protein, (ii) a first protein probe specific for a first region of said at least one protein, where the first protein probe contains a capture region, (iii) a second protein probe specific for a second region of the at least one protein, where the second protein probe contains a nanoreporter comprising a plurality of different detectable labels, and (iv) a matrix having attached thereto a moiety which is capable of binding to the capture region in the first protein probe; (b) forming at least a complex comprising the at least one protein, the first protein probe, the second protein probe and the moiety, where the at least one protein is bound to the first and second protein probes, and where the moiety is bound to the capture probe in the first protein probe; and (c) individually detecting the complex or at least part of the complex by a method comprising individually counting the presence of one or more molecules of the nanoreporter where the presence of the one or more molecules is indicative of the concentration of the protein in the sample. In some embodiments, the individually detecting further comprises detecting a digital signal.

A moiety refers to and is also known as an entity. A moiety of the invention is operably linked to a matrix and binds with a capture region of a first protein probe. The moiety is operably linked to the matrix by a physical or chemical bond, including, but not limited to, a covalent bond, a non-covalent bond, an electron bond, a bent bond, an aromatic bond, a metallic bond, a hydrogen bond, an ionic bond, or van der Waals forces. The moiety binds with a capture region of a first protein probe through any of the physical or chemical bonds described herein, receptor-ligand interactions, hybridization events between two oligonucleotides, or interactions between an oligonucleotide and a polypeptide. For example, a capture region that contains biotin binds to a moiety containing streptavidin, forming a strong non-covalent bond, wherein a matrix having attached to the streptavidin, permits the matrix to bind to the capture region of the first protein probe (see, FIG. 1). While all known receptor-ligand interactions are contemplated, those interactions with a dissociation constant (Kd) of between 0.1 fM and 1000 nM are preferred. Hybridization events occur between oligonucleotides having complementary sequences, however, perfect or complete complementarity is not required. The invention encompasses those hybridization events between oligonucleotides having 50%, 60%, 70%, 80%, 90%, 95%, 100%, and any percentage complementarity in between. Furthermore, the association of an aptamer with a first protein probe provides a non-limiting example of a preferred interaction between an oligonucleotide and a polypeptide.

In some embodiments, the invention provides methods for determining the concentration of a plurality of target proteins by forming a plurality of complexes, each complex comprising (i) at least one target protein (ii) a first protein probe specific for a first region of the at least one protein, where the first protein probe comprises a capture region (iii) a second protein probe specific for a second region of the at least one protein, where the second protein probe comprises a nanoreporter comprising a plurality of different detectable labels and (iv) a moiety attached to a matrix, where the moiety is capable of binding to the capture region in the first protein probe, where each second protein probe comprises a different nanoreporter region. In some embodiments, each nanoreporter in the plurality of complexes has a detectable signal that distinguishes it from other nanoreporters in the population. In some embodiments, the dissociation constant of the first and the second protein probes is about $1.00 \times 10^{-10}$ to about $1.00 \times 10^{-08}$. In some embodiments, the concentration of two or more target proteins is determined. In some embodiments, the concentration of 3, 4, 5, 10, 20, 30, 50, 100, 200, 300, 500, 600, 700, 800, 900, 1000 or more than 1000 different target proteins is determined. In some embodiments, the concentration of at least 972 different target proteins is determined.

In some embodiments, the matrix is selected from the group consisting of a bead and an array. In some embodiments, the matrix is a bead. In some embodiments where a plurality of target proteins is analyzed, the matrix is a bead and each moiety in each complex of the plurality of complex is attached to a different bead. In some embodiments, the matrix is a surface. In some embodiments where a plurality of target proteins is analyzed, the matrix is a surface and each moiety in each complex of the plurality of complex is attached to a different location of the surface.

In some embodiments, the first protein probe and the second protein probe are independently selected from the group consisting of antibody, peptide, aptamer and peptoid.

In some embodiments, the nanoreporter comprises a single-stranded nucleic acid backbone, the backbone comprising a plurality of label attachment regions covalently attached together in a linear combination, where each label attachment region is hybridized to a complementary polynucleotide sequence having attached thereto the detectable label. In some embodiments, the nanoreporter is attached to the second probe through hybridization to a linker oligo. In some embodiments, the nanoreporter is hybridized to the linker oligo at a temperature of about 32 degrees Celsius (° C.) to about 40° C. In some embodiments, the nanoreporter is hybridized to the linker oligo at a temperature of about 37° C. In some embodiments, the nanoreporter comprises a portion that is complementary to the linker oligo. In some embodiments, the complementary region is about 15 to about 20 bases.

In some embodiments, the invention provides methods for determining the concentration of at least one protein in a sample comprising the steps of: (a) providing: (i) at least one protein, (ii) a first protein probe specific for a first region of the at least one protein, where the first protein probe is attached to a first capture region or a first matrix, (iii) a second protein probe specific for a second region of the at least one protein, where the second protein probe comprises a signal oligo, and (iv) when the first probe is attached to a first capture region: a second matrix having attached thereto a moiety which is capable of binding to the capture region in the first protein probe; (b) forming at least a first complex comprising the at least one protein, the first protein probe, and the second protein probe, where the at least one protein is bound to the first and second protein probes, and where when the first probe is attached to a first capture region the capture probe is bound to the moiety in the second matrix; (c) releasing the signal oligo from the first complex; (d) forming a second complex comprising: (1) at least the signal oligo and (2) at least one oligo probe comprising a signal oligo-specific region and a region comprising a nanoreporter where the nanoreporter comprises a plurality of different detectable labels; and (e) individually detecting the second complex or at least part of the second complex by a method comprising individually counting the presence of one or more molecules of the nanoreporter, where the presence of the second one or more molecules is indicative of the concentration of the protein in the sample. In some embodiments, individually detecting further comprises detecting a digital signal.

In some embodiments, the first matrix is a bead or an array. Preferably, the first matrix is a bead. In other embodiments, the second matrix is a bead or an array.

In some embodiments, the signal oligo is attached to a second capture region. In some embodiments, the releasing of the signal oligo further comprises capturing directly or indirectly the signal molecule into a third matrix.

In some embodiments, the nanoreporter further comprises a constant region, where the constant region comprises a plurality of repeat nucleotide sequences. In some embodiments, the constant region is bound to a second moiety in a third matrix, where the second moiety is capable of binding the constant region.

In some embodiments, the invention provides methods for determining the concentration of a plurality of target proteins by forming a plurality of complexes, each complex comprising (i) at least one target protein (ii) a first protein probe specific for a first region of the at least one protein, where the first protein probe is attached to a capture region or a first matrix (iii) a second protein probe specific for a second region of the at least one protein, where the second protein probe comprises a signal molecule, where when the first probe is attached to a first capture region the capture probe is bound to the moiety in the second matrix, and where each second protein probe in each the plurality of complexes comprises a different signal oligo. In some embodiments, the concentration of two or more target proteins is determined. In some embodiments, the concentration of 2, 3, 4, 5, 10, 20, 30, 50, 100, 200, 300, 500, 600, 700, 800, 900, 1000 or more than 1000 different target proteins is determined. In some embodiments, the concentration of at least 972 different target proteins is determined.

In some embodiments, the first matrix of the complex of the plurality of complexes is a bead and the bead comprises a plurality of identical first protein probes. The term identical is meant to describe a protein probe having the same sequence and either containing or attaching to the same capture region.

In some embodiments, the first protein probe and the second protein probe are independently selected from the group consisting of antibody, peptide, aptamer and peptoid.

In some embodiments, the nanoreporter comprises a single-stranded nucleic acid backbone, the backbone comprising a plurality of label attachment regions covalently attached together in a linear combination, where each label attachment region is hybridized to a complementary polynucleotide sequence having attached thereto the detectable label.

In some embodiments, the invention provides methods for determining the concentration of at least one protein in a sample comprising the steps of: (a) providing: (i) at least one protein, (ii) a first protein probe specific for a first region of the at least one protein, where the first protein probe is attached to a first oligo, and (iii) a second protein probe specific for a second region of the at least one protein, where the second protein probe is attached to a second oligo; (b) forming a first complex comprising the at least one protein, the first protein probe and the second protein probe, where the at least one protein is bound to the first and second protein probes; (c) ligating the first and the second oligo to form a signal oligo; (d) forming a second complex comprising: (1) the first signal oligo and (2) at least one oligo probe comprising a signal oligo-specific region and a region comprising a nanoreporter where the nanoreporter comprises a plurality of different detectable labels; and (e) individually detecting the second complex or at least part of the second complex by a method comprising individually counting the presence of one or more molecules of the nanoreporter, where the presence of the one or more molecules is indicative of the concentration of the protein in the sample. In some embodiments, the individually detecting further comprises detecting a digital signal.

In some embodiments, the signal oligo is released from the first complex. In some embodiments, the signal oligo comprises a capture region. In some embodiments, the releasing of the signal oligo further comprises capturing directly or indirectly the signal oligo into a matrix.

In some embodiments, the invention provides methods determining the concentration of a plurality of target proteins by forming a plurality of complexes, each complex comprising (i) at least one target protein, (ii) a first protein probe specific for a first region of the at least one protein, where the first protein probe is attached to a first oligo (iii) a second protein probe specific for a second region of the at least one protein, where the second protein probe is attached to a second oligo, where the ligation of the first oligo and the second oligo form a signal oligo, and where each complex in the plurality of complexes comprises a different signal oligo. In some embodiments, the concentration of two or more target proteins is determined. In some embodiments, the concentration of 2, 3, 4, 5, 10, 20, 30, 50, 100, 200, 300, 500, 600, 700, 800, 900, 1000 or more than 1000 different target proteins is determined. In some embodiments, the concentration of at least 972 different target proteins is determined.

In some embodiments, the first protein probe and the second protein probe are independently selected from the group consisting of antibody, peptide, aptamer and peptoid.

In some embodiments, the nanoreporter comprises a single-stranded nucleic acid backbone, the backbone comprising a plurality of label attachment regions covalently attached together in a linear combination, where each label attachment region is hybridized to a complementary polynucleotide sequence having attached thereto the detectable label.

In some embodiments, the invention provides a population of uniquely labeled protein probes, where each probe comprises: i) a target-specific region; and ii) a region comprising a nanoreporter comprising a plurality of different detectable molecules, where the nanoreporter in each protein probe has a detectable signal that distinguishes it from other nanoreporters in the population. In some embodiments, the target-specific region is selected from the group consisting of antibody, peptide, aptamer and peptoid.

In some embodiments, the nanoreporter comprises a single-stranded nucleic acid backbone, the backbone comprising a plurality of label attachment regions covalently attached together in a linear combination, where each label attachment region is hybridized to a complementary polynucleotide sequence having attached thereto the detectable label. In some embodiments, the dissociation constant of the target specific region is about $1.00 \times 10^{-10}$ to about $1.00 \times 10^{-8}$.

In some embodiments, the nanoreporter is attached to the protein probe through hybridization to a linker oligo. In some embodiments, the nanoreporter is hybridized to the linker oligo at a temperature of about 32° C. to about 40° C. In some embodiments, the nanoreporter is hybridized to the linker oligo at a temperature of about 37° C. In some embodiments, the nanoreporter comprises a portion that is complementary to the linker oligo. In some embodiments, the complementary region is about 15 to about 20 bases.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The patent or application file contains at least one drawing executed in color. Copies of this patent or patent application publication with color drawings will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9 is a schematic diagram depicting certain embodiments of the invention using proximity ligation. The label monomers of the nanoreporter (depicted as circles) emit individual signals of qualitatively different wavelengths that are spatially-distinguishable and are, from left to right positions, red (R), yellow (Y), green (G), blue (B), red (R), and violet (V).

DETAILED DESCRIPTION OF THE INVENTION

Figure 1:
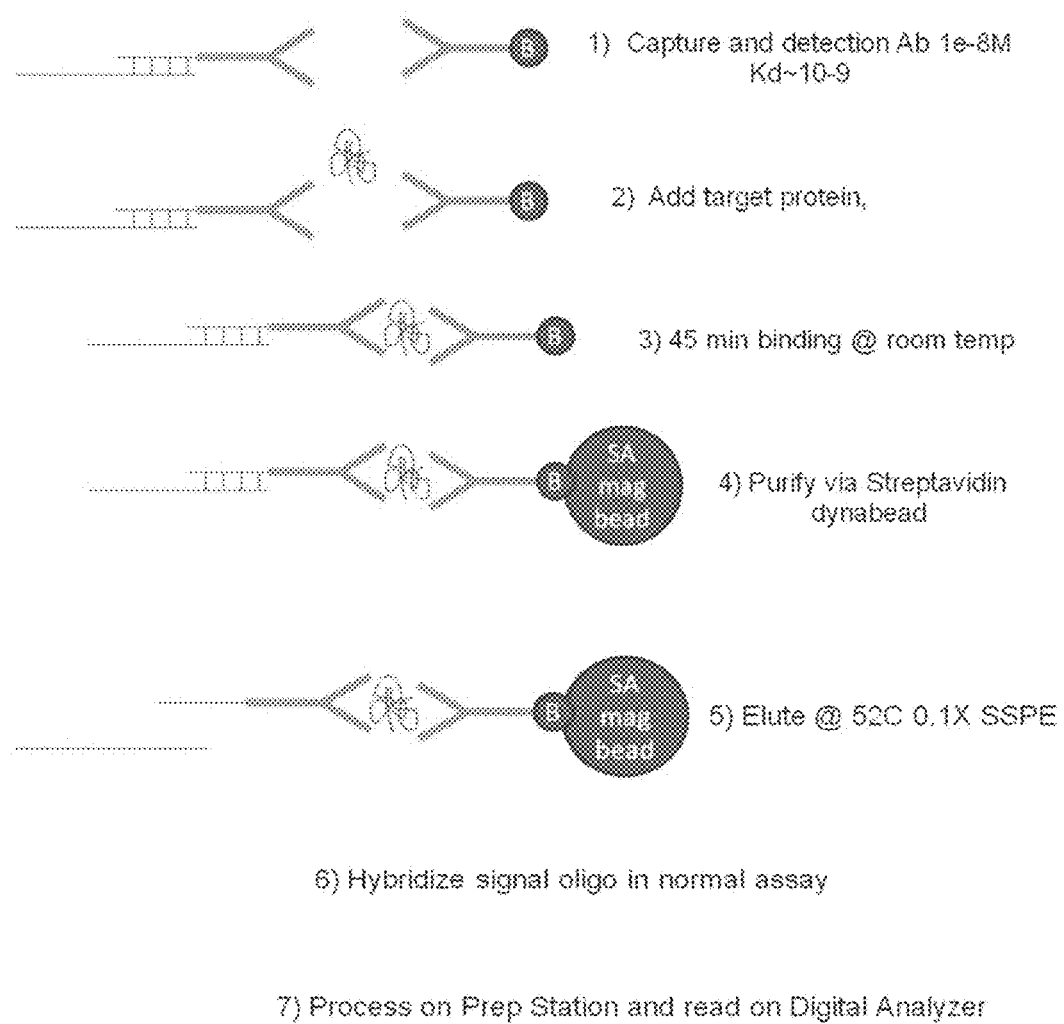
FIG. 1 is a schematic diagram depicting one embodiment of the invention in which two antibodies specific for a target protein bind to the target protein in solution. The first antibody is attached to an affinity tag such as biotin (depicted as a circle labeled "B"), while the second antibody is attached to a partially double stranded nucleic acid probe. The binding of the first and second antibodies to the target protein forms a complex that is isolated from the solution via the affinity tag of the first antibody. One of the strands of the partially double stranded nucleic acid probe can be eluted to generate a signal oligo, which can then be analyzed by any the methods described herein.

Reference will now be made in detail to particularly preferred embodiments of the invention. Examples of the preferred embodiments are illustrated in the following Examples section.

Unless defined otherwise, all technical and scientific terms used herein have the same meaning as is commonly understood by one of skill in the art to which this invention belongs. All patents and publications referred to herein are incorporated by reference in their entirety.

The present invention provides compositions and methods for detection and quantification of individual target molecules in biomolecular samples. In particular, the invention provides protein probes that are capable of binding individual target molecules. The invention also provides the use of nanoreporters. Through nanoreporters' label codes, the binding of the protein probes to target molecules results in the identification of the target molecules. Methods of making and using such protein probes and/or nanoreporters are also provided. The methods and compositions described herein can be used in a wide variety of applications such as diagnostic, prognostic, quality control and screening applications.

Certain aspects of the invention relate to the detection of multiple target molecules. Multiplexing is the measurement of more than one target molecule within a sample without having to split the sample. The methods described herein provide potential benefits in the areas of multiplexing, quantification, and sensitivity. For example, in some embodiments the target molecule is a protein. Measurement of protein concentrations is challenging. Proteins are sticky and tend to aggregate. In addition proteins are unstable, and tend to unfold easier than RNA or DNA. Extremes in pH, temperatures, solute concentration, and the presence of denaturants are conditions that can interrupt protein stability and complicate measurement. In some embodiments, the invention provides methods and compositions for multiplexed protein measurements that are sensitive and reliable.

Multiplexing within a fluid sample is a key advantage of this approach. Multiplexing within one sample saves significant labor, reduces sample quantity requirements proportional to the number of measurements, and improves accuracy by elimination of errors compounded by separate sample handling and measurement steps. In some embodiments, the methods described herein allow for the pooling of different samples together during processing to be analyzed at once. This offers throughput advantages and can accelerate the analysis of different samples, e.g., up to eight times.

In some embodiments, the invention provides protein probes for the analysis of target molecules. In some embodiments, the invention provides a protein probe population for use in a multiplexed assay. Each protein probe in the population is specific for a target molecule. The binding of the target molecules to the proteins probes is then detected using nanoreporters. Each nanoreporter comprises a unique label code that can be associated to a specific target molecule.

In some embodiments, the nanoreporters are attached, directly or indirectly, to the protein probes. A unique nanoreporter's label code is then assigned to a specific protein probe such that each nanoreporter's label code can be associated to the target molecule bound to the protein probe.

In other embodiments, the protein probes are attached, directly or indirectly, to a signal oligo. Each protein probe is attached to a unique signal oligo. The nanoreporters used for the analysis of the signal oligo comprise a portion that is complementary to the signal oligo. A unique nanoreporter's label code is assigned to a specific signal oligo sequence such that each nanoreporter's label code can be associated to the target molecule via the signal oligo sequence.

In other aspect of the invention, the invention provides methods for detecting target molecules by measuring signals digitally. Current technologies use analogue fluorescent signals to quantify the presence of target molecules. Quantification using fluorescence can be error prone for a variety of reasons. For example, fluorophores can photobleach. There can be changes in the spectra in the presence of proteins or due to local environment, e.g., pH, salt. In addition, the light sources can vary in intensity over time. For example, arc lamps, a commonly used light source, demonstrate a phenomenon called arc wander that can cause significantly different illumination levels over time. In embodiments of the invention, the target molecules are detected digitally. While fluorescence might be used to read the nanoreporter's label code, the signals are high and the spot is either present of not, thus the digital detection. The digital detection of target molecules leads to more accurate quantification.

Protein Probes

Protein probes are molecules or assemblies that are designed to bind with at least one target protein, at least one target protein surrogate, or both; and can, under appropriate conditions, form a molecular complex comprising the protein probe and the target protein. The terms "protein", "polypeptide", "peptide", and "amino acid sequence" are used interchangeably herein to refer to polymers of amino acids of any length. The polymer may be linear or branched, it may comprise modified amino acids, and it may be interrupted by non-amino acids or synthetic amino acids. The terms also encompass an amino acid polymer that has been modified, for example, by disulfide bond formation, glycosylation, lipidation, acetylation, phosphorylation, or any other manipulation, such as conjugation with a labeling component. As used herein the term "amino acid" refers to either natural and/or unnatural or synthetic amino acids, including but not limited to glycine and both the D or L optical isomers, and amino acid analogs and peptidomimetics.

The methods of the invention also encompassed protein probes designed to bind targets other than proteins. Examples of target other than proteins include, but are not limited to, nucleic acids, lipids, carbohydrates, ions, small molecules, organic monomers, and drugs. For convenience only, most of the embodiments described herein are explained in the context of protein probes that bind to a target protein. However, these embodiments also can be applied to other target molecules.

Protein probes typically are part of at least one probe set, comprising at least one first probe and at least one second probe. In certain embodiments, however, at least one probe set can comprise only first probes or second probes, but not both first probes and second probes. Probes comprise at least one reaction portion that allow them to bind to or interact with at least one target protein, at least one part of at least one target protein, at least one target protein surrogate, at least part of a target protein surrogate, or combinations thereof; typically in a sequence-specific, a confirmation-specific manner, or both; for example but not limited to antigen-antibody binding, aptamer-target binding, and the like.

In certain embodiments, the protein probes comprise an identity portion or at least part of an identity portion, for example, a signal oligo, a nanoreporter and/or linker oligo. In certain embodiments, the protein probes comprise a capture region. In some embodiments, the capture region is used for the isolation of the protein probe and/or immobilization of the protein probe into a surface. The capture region can be an affinity tag as described below, a bead, a slide or an array.

In some embodiments, the protein probe is an antibody. As used herein, the terms antibody and antibodies are used in a broad sense, to include not only intact antibody molecules, for example but not limited to immunoglobulin A, immunoglobulin G and immunoglobulin M, but also any immunoreactive component(s) of an antibody molecule that immunospecifically bind to at least one epitope. Such immunoreactive components include but are not limited to, Fab fragments, Fab' fragments, F(ab')$_2$ fragments, single chain antibody fragments (scFv), miniantibodies, diabodies, cross-linked antibody fragments, Affibody™, cyclotides, molecules, and the like. Immunoreactive products derived using antibody engineering or protein engineering techniques are also expressly within the meaning of the term antibodies. Detailed descriptions of antibody and/or protein engineering, including relevant protocols, can be found in, among other places, J. Maynard and G. Georgiou, Ann. Rev. Biomed. Eng. 2:339 76 (2000); Antibody Engineering, R. Kontermann and S. Dubel, eds., Springer Lab Manual, Springer Verlag (2001); U.S. Pat. No. 5,831,012; and S. Paul, Antibody Engineering Protocols, Humana Press (1995).

The skilled artisan will appreciate that antibody can be obtained from a variety of sources, including but not limited to polyclonal antibody, monoclonal antibody, monospecific antibody, recombinantly expressed antibody, humanized antibody, plantibodies, and the like; and can be obtained from a variety of animal species, including rabbit, mouse, goat, rat, human, horse, bovine, guinea pig, chicken, sheep, donkey, human, and the like. A wide variety of antibody is commercially available and custom-made antibody can be obtained from a number of contract labs. Detailed descriptions of antibodies, including relevant protocols, can be found in, among other places, Current Protocols in Immunology, Coligan et al., eds., John Wiley & Sons (1999, including updates through August 2003); The Electronic Notebook; Basic Methods in Antibody Production and Characterization, G. Howard and D. Bethel, eds., CRC Press (2000); J. Goding, Monoclonal Antibodies: Principles and Practice, 3d Ed., Academic Press (1996); E. Harlow and D. Lane, Using Antibodies, Cold Spring Harbor Lab Press (1999); P. Shepherd and C. Dean, Monoclonal Antibodies: A Practical Approach, Oxford University Press (2000); A.

Johnstone and M. Turner, Immunochemistry 1 and 2, Oxford University Press (1997); C. Borrebaeck, Antibody Engineering, 2d ed., Oxford university Press (1995); A. Johnstone and R. Thorpe, Immunochemistry in Practice, Blackwell Science, Ltd. (1996); H. Zola, Monoclonal Antibodies: Preparation and Use of Monoclonal Antibodies and Engineered Antibody Derivatives (Basics: From Background to Bench), Springer Verlag (2000); and S. Hockfield et al., Selected Methods for Antibody and Nucleic Acid Probes, Cold Spring Harbor Lab Press (1993). Additionally, a vast number of commercially available antibodies, including labeled or unlabeled; polyclonal, monoclonal, and monospecific antibodies, as well as immunoreactive components thereof; custom antibody suppliers, and the like can be found on the World Wide Web at, among other places, the Antibody Search page at biocompare.com, the Antibody Resource Page at antibodyresource.com, and the Antibody Explorer page at sigmaaldrich.com.

In some embodiments, the antibodies described herein are attached to a nucleic acid, e.g., signal oligo, linker oligo and/or nanoreporter. Methods to attach nucleic acids to antibodies are known in the art. Any suitable method to attach nucleic acids to antibodies is encompassed in the methods of the invention. The antibodies described herein can be attached to a nucleic acid by the methods described in Gullberg et al., PNAS 101 (22): pages 228420-8424 (2004); and Boozer et al, Analytical Chemistry, 76(23): pages 6967-6972 (2004), both incorporated herein by reference. The antibodies described herein can be attached to a nucleic acid by random amine attachment. In some embodiments, the antibodies described herein can be attached to a nucleic acid by random amine attachment using a 10 to 1 ratio of nucleic acid to antibody. The antibodies described herein can be attached to a nucleic acid by the methods described in Kozlov et al., Biopolymers 5: 73 (5): pages 621-630 (2004) incorporated herein by reference. The antibodies described herein can be attached to a nucleic acid by hydrazine chemistry. The antibodies described herein can be attached to a nucleic acid using tadpoles as described in Nolan, Nature Methods 2, 11-12 (2005), incorporated herein by reference. The antibodies described herein can be attached to a nucleic acid by any suitable methods known in the art to generate engineered antibodies including the ones described herein.

In some embodiments, the protein probe is an aptamer. Aptamers include nucleic acid aptamers (i.e., single-stranded DNA molecules or single-stranded RNA molecules) and peptide aptamers. Aptamers bind target molecules in a highly specific, conformation-dependent manner, typically with very high affinity, although aptamers with lower binding affinity can be selected if desired. Aptamers have been shown to distinguish between targets based on very small structural differences such as the presence or absence of a methyl or hydroxyl group and certain aptamers can distinguish between D- and L-enantiomers. Aptamers have been obtained that bind small molecular targets, including drugs, metal ions, and organic dyes, peptides, biotin, and proteins, including but not limited to streptavidin, VEGF, and viral proteins. Aptamers have been shown to retain functional activity after biotinylation, fluorescein labeling, and when attached to glass surfaces and microspheres.

Nucleic acid aptamers, including speigelmers, are identified by an in vitro selection process known as systematic evolution of ligands by exponential amplification (SELEX). In the SELEX process very large combinatorial libraries of oligonucleotides, for example $10^{14}$ to $10^{15}$ individual sequences, often as large as 60-100 nucleotides long, are routinely screened by an iterative process of in vitro selection and amplification. Most targets are affinity enriched within 8-15 cycles and the process has been automated allowing for faster aptamer isolation. Peptide aptamers are typically identified by several different protein engineering techniques known in the art, including but not limited to, phage display, ribosome display, mRNA display, selectively infected phage technology (SIP), and the like. The skilled artisan will understand that nucleic acid aptamers and peptide aptamers can be obtained following conventional procedures and without undue experimentation. Detailed descriptions of aptamers, including relevant protocols, can be found in, among other places, L. Gold, J. Biol. Chem., 270(23):13581 84 (1995); S. Jayasena, Clin. Chem., 45:1628-50 (1999); V. Sieber et al., Nat Biotechnol. 16 (10):955-60 (1998); D. Wilson and J. Szostak, Ann. Rev. Biochem. 68:611-47 (1999); L. Jermutus et al., Eur. Biophys. J., 31:179-84 (2002); S S. Spada et al., Biol. Chem., 378:445-56 (1997); B. Wlotzka et al., Proc. Natl. Acad. Sci., 99:8898-8902 (2002).

In some embodiments the aptamer will be ligated or hybridized to a signal oligo, a linker oligo and/or a nanoreporter. In some embodiments, the ligation of the aptamer to a nanoreporter is done before annealing segments with labels to the nanoreporters. The hybridization or ligation of aptamers can be done by any suitable method known in art. For example ligation can be performed enzymatically by at least one DNA ligase or at least one RNA ligase, for example but not limited to, T4 DNA ligase, T4 RNA ligase, *Thermus thermophilus* (Tth) ligase, *Thermus aquaticus* (Taq) DNA ligase, or *Pyrococcus furiosus* (Pfu) ligase. Ligation can also be performed by chemical ligation can, using activating and reducing agents such as carbodiimide, cyanogen bromide (BrCN), imidazole, 1-methylimidazole/carbodiimide/cystamine, N-cyanoimidazole, dithiothreitol (DTT) and ultraviolet light.

In some embodiments, the protein probe is a peptoid. Peptoids are short sequences of N-substituted glycines synthetic peptides that bind proteins. In some embodiments, small size peptoids improve diffusion and kinetics of the methods described herein. Any suitable method known in the art to generate peptoids is encompassed in the methods described herein. See Simon et al., PNAS 15; 89(20): 9367-9371 (1992), incorporated herein by reference.

Target Proteins

Target proteins are the protein detected or measured by binding of a protein probe whose target-specific region(s) recognize thereto. However, the invention encompasses detection of other targets beyond proteins such as nucleic acid, a lipid, a carbohydrate, a small molecule, an organic monomer, or a drug. Nucleic acids that can be analyzed by the methods herein include: double-stranded DNA, single-stranded DNA, single-stranded DNA hairpins, DNA/RNA hybrids, RNA (e.g., mRNA or miRNA) and RNA hairpins. For convenience only, the methods described herein are explained mostly in the context of analyzing proteins. However, the embodiments described herein also can be used to detect non-protein targets.

A target protein can be part of a biomolecular sample that contains other components or can be the sole or major component of the sample. A target protein can be a component of a whole cell or tissue, a cell or tissue extract, a fractionated lysate thereof or a substantially purified molecule. The target protein can be attached in solution or solid-phase, including, for example, to a solid surface such as a chip, microarray or bead. Also the target molecule can have either a known or unknown structure or sequence.

The compositions, methods, and kits disclosed herein can also be used in a wide variety of applications to determine the presence of target proteins in a sample. For example but without limitation, the compositions, methods, and kits are useful for, pharmacokinetic studies, including but not limited to, drug metabolism, ADME profiling, and toxicity studies; target validation for drug discovery; protein expression profiling; proteome analyses; metabolomic studies; post-translation modification studies, including but not limited to glycosylation, phosphorylation, acetylation, and amino acid modification, such as modification of glutamate to form gamma-carboxy glutamate and hydroxylation of proline to form hydroxylation; analyses of specific serum or mucosal antibody levels; evaluation of non-nucleic acid diagnostic indicators; foreign antigen detection; and the like.

In certain embodiment, at least one first protein probe, at least one second protein probe, or both the first protein probe and the second protein probe of at least one probe set comprise at least one antibody, aptamer or peptoid that reacts specifically with at least one target protein or at least one target protein surrogate. In certain embodiments, at least one first protein probe, at least one second protein probe, or both the first protein probe and the second protein probe of at least one probe set comprise binding proteins that specifically interact with at least one target protein or at least one target protein surrogate.

The skilled artisan understands that with antibody probes, the reactive portion typically comprises the antigen binding site and related residues of the antibody molecule; and the target sequences comprise that portion of the analyte that includes the epitope, whether such sequences are linear, conformational, or combinations thereof. The skilled artisan will appreciate that the molecular complexes and the at least part of the molecular complexes described herein can be individually detected while tethered or attached to a substrate or while in solution, depending on, among other things, the nature of the specific molecular complex or cleavable component and the SMD technique and detection apparatus employed.

Protein isolation techniques are also well known in the art and kits employing at least some of these techniques are commercially available. Protein isolation techniques typically employ one or more of the following: maceration and cell lysis, including physical, chemical and enzymatic methods; centrifugation; separations by molecular weight, such as size exclusion chromatography and preparative electrophoresis; selective precipitation, for example, salting-in and salting-out procedures; various chromatographic methods; and the like. Detailed descriptions of and relevant protocols for protein purification techniques can be found in, among other places, Marchak et al., Strategies for Protein Purification and Characterization: A Laboratory Course Manual, Cold Spring Harbor Press (1996); Essentials from Cells: A Laboratory Manual, D. Spector and R. Goldman, eds., Cold Spring Harbor Press (2003); R. Simpson, Proteins and Proteomics: A Laboratory Manual, Cold Spring Harbor Press (2003); and D. Liebler, Introduction to Proteomics, Humana Press (2002). Commercially available kits can also be used, for example but not limited to, ProteoExtract™ Partial Proteome Extraction Kits (P-PEK) and ProteoExtract™ Complete Proteome Extraction Kits (C-PEK), available from CALBIOCHEM™, La Jolla, Calif. The skilled artisan will appreciate that non-nucleic acid analytes for use with the inventive compositions, methods, and kits can be readily obtained without undue experimentation using such purification techniques and commercial kits.

Methods

The present invention provides methods for detection and quantification of individual target proteins in biomolecular samples. In particular, the invention provides protein probes that are capable of binding individual target proteins. The invention also provides the use of nanoreporters. Through nanoreporters' label codes, the binding of the protein probes to target proteins results in the identification of the target proteins. Methods of making and using such protein probes and/or nanoreporters are also provided.

In some embodiments, the invention provides methods for detection and/or quantification of a target protein by binding a protein probe to a target protein. A protein probe comprises at least one reaction portion that allow the probe to bind to or interact with the target protein or a target protein surrogate or combinations thereof; typically in a sequence-specific, a confirmation-specific manner, or both; for example but not limited to antigen-antibody binding, aptamer-target binding, and the like.

Protein probes typically are part of at least one probe set, comprising at least one first probe and at least one second probe. Thus, in some embodiments the invention provides methods for detection and/or quantification of a target protein by binding a protein probe set to a target protein, where the protein probe set comprises a first protein probe and a second protein probe. The first protein probe and the second protein probe comprise at least one reaction portion that allow the probes to bind to or interact with different regions of the target protein or a target protein surrogate or combinations thereof, e.g., in a sequence-specific manner, a confirmation-specific manner, or both.

In some embodiments, the methods described herein further comprise protein probes containing an identity portion or at least part of an identity portion, for example, a signal oligo, a nanoreporter and/or linker oligo. The identity portion allows for the identification of the presence or absence of the protein probe or probes bound to the target protein in the detection step of the methods described herein. Thus, in some embodiments the invention provides methods for detection and/or quantification of a target protein by binding the protein probe or protein probe set to a target protein, wherein the protein probe or at least one of the protein probes in the probe set contains an identity portion (e.g., a signal oligo, a nanoreporter and/or linker oligo).

In some embodiments, the identity portion is a signal oligo. A signal oligo comprises a polynucleotide sequence. Each protein probe or protein probe set will have a specific and/or unique signal oligo in an assay, such that the signal oligo can be associated with the target protein. In certain embodiments, the signal oligo comprises about 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70 or more nucleotide bases In one embodiment, the signal oligo comprises between 40 to 120 bases, or between 80 and 100 bases. In some embodiments, the signal oligo is bioatinylated and used with a capture probe and a nanoreporter as described below. The signal oligo can be attached directly or indirectly to the protein probe. Methods for attaching nucleic acid to proteins probes are known in art including those described herein. Signal oligos can be a designed synthetic nucleic acid sequences or a natural sequence derived from a natural source such as sequence from viral genome, bacteriophages, or animal genomes.

In some embodiments, the signal oligo is attached indirectly to a protein probe through hybridization with a linker oligo attached to the protein probe. A linker oligo comprises a polynucleotide sequence. In the embodiments in which a linker oligo is used, each linker oligos will be specific and/or unique for a protein probe or protein probe set in an assay such that the complementary signal oligo can be associated to the target protein. The signal oligo comprises a portion that is complementary to the linker oligo attached to the protein probe. In some embodiments, the complementary portion of the signal oligo is 5, 6, 7, 8, 9, 10, 11, 12, 13, 14, 15, 16, 17, 18, 19, 20, 21, 22, 23, 24, 25, 26, 27, 28, 29, 30, 40, 50, 60, 70 or more nucleotide bases. In some embodiments, the complementary portion of the signal oligo is 10-25 bases. In some embodiments, the complementary portion of the signal oligo is in the range of 15-20 bases. In some embodiments, the complementary portion of the signal oligo is 40 bases. In some embodiments, the complementary portion of the signal oligo is 30 bases. In some embodiments, the complementary portion of the signal oligo is 20 bases. The linker oligo can be a designed synthetic nucleic acid sequences or a natural sequence derived from a natural source such as a sequence from viral genome, bacteriophages, or animal genomes.

FIG. 1 shows a schematic representation of one of the embodiments of the invention in which a signal oligo is used for the detection of the target protein. The embodiment depicted in FIG. 1 is set up to separate the binding of the target protein from the hybridization of the nanoreporters. FIG. 1 in step 1) shows a first protein probe comprising a signal oligo attached to the probe via hybridization with a linker oligo; and a second protein attached to an affinity tag. In the embodiment depicted in FIG. 1 the protein probes are antibodies and the affinity tag is biotin. However, the embodiment depicted in this figure can utilize any of the protein probes and affinity tags described herein. Both the first and second protein probes comprise a target specific region capable of binding one or more portions of a target. In step 2) and 3), the target protein is mixed with the first and second protein probes. In step 4), the complex of target protein and protein probes is purified. In the example depicted in FIG. 1 the complex of target protein and protein probes is purified using streptavidin-coupled magnetic beads, such as Dynabeads® (Invitrogen). However, in this or any other embodiment described herein, the complex of target protein and protein probe (s) can be purified by any suitable method known in the art such as chromatography, including but not limited to HPLC, FPLC, size exclusion (gel filtration) chromatography, affinity chromatography, ion exchange chromatography, hydrophobic interaction chromatography, immunoaffinity chromatography, and reverse phase chromatography; ligand-receptor binding, such as biotin-avidin, maltose-maltose binding protein (MBP), calcium-calcium binding peptide; aptamer-target binding; zip code hybridization; and the like.

In step 5) of FIG. 1, the signal oligo is eluted from the complex of target protein and protein probes and analyzed using nanoreporters as described below. Methods for eluting the signal oligos are known in the art including the ones depicted in FIG. 1 and described herein. In some embodiments, the methods depicted in FIG. 1 are used to detect and/or quantify a plurality of target proteins. Each target protein will be detected by a probe set comprising a first probe and a second probe as described in FIG. 1. Each probe set will have a specific and/or unique signal oligo that can then be associated to the target protein of each probe set.

In some embodiments, the protein probes comprise a capture region. In some embodiments, the capture region is used for the isolation of the protein probe and/or immobilization of the protein probe into a surface. The capture region can be an affinity tag as described below or a solid surface such as bead, a slide or an array.

Figure 6:
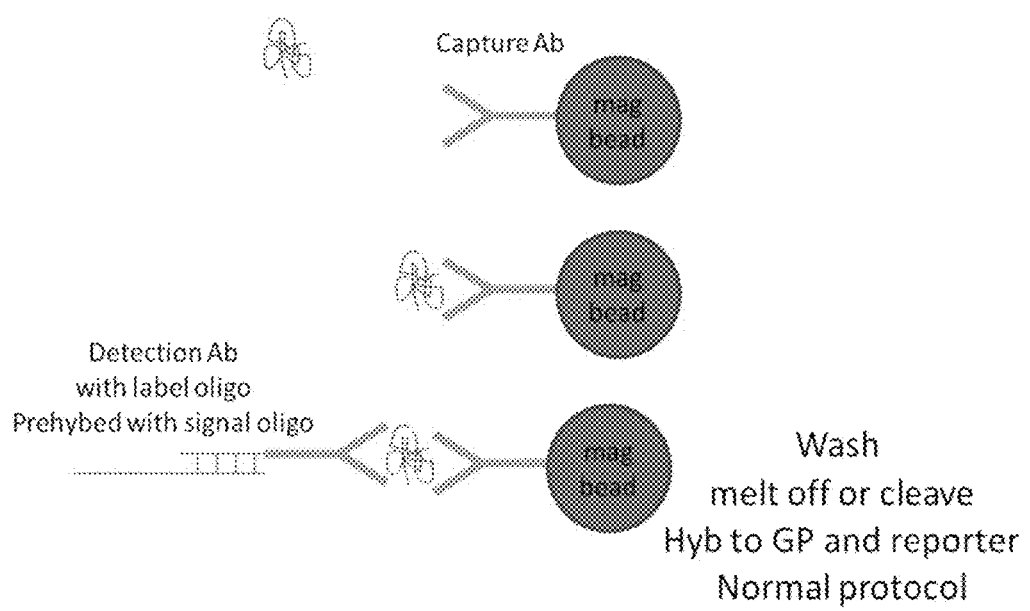
FIG. 6 is a schematic diagram depicting an embodiment of the invention in which a capture antibody specific for a target protein binds to the target protein in solution to form a complex. The complex can then be isolated from the solution. The complex is then contacted with a second antibody, where the second antibody is attached to a partially double stranded nucleic acid probe. One of the strands of the partially double stranded nucleic acid probe can be eluted to generate a signal oligo that may be analyzed by any the methods described herein.

FIG. 6 shows a schematic representation of one of the embodiments of the invention. In this embodiment a protein probe is attached to a capture region, e.g., a magnetic bead. FIG. 6 depicts the use of an antibody. However, the embodiment depicted in this figure can utilize any of the protein probes and capture regions described herein. The protein probes (e.g., antibodies) can be attached to a capture region by any suitable method knows in the art including the methods described herein. The target protein is mixed with the protein probe containing the capture region. The complex of target protein and protein probe is then contacted with a second protein probe attached to a signal oligo via a linker oligo. The complex of target protein and protein probes are purified. In this example, the complex of target protein and antibody is purified using the magnetic bead in the capture antibody. However, in this or any other embodiment described herein, the complex of target protein and protein probes can be purified by any suitable method known in art such as the methods described above. If the capture region is a slide or an array, the complex of target protein and protein probes can be purified by washing off the excess of unbound sample and protein probes. The isolated target protein/protein probes complex is then washed and the signal oligo is eluted. The signal oligo is analyzed using nanoreporters as described below. Methods for eluting the signal oligos are known in the art including the methods described herein. In this embodiment, the proteins and nanoreporters are largely separate, which eliminates concerns about protein stickiness. In some embodiments, the methods depicted in FIG. 6 are used to detect and/or quantify a plurality of target proteins. Each target protein will be detected by a probe set comprising a first probe and a second probe as described in FIG. 6. Each probe set will have a specific and/or unique signal oligo that can then be associated to the target protein of each probe set.

In some embodiments, the signal oligo is attached to an affinity tag. The affinity tag in the signal oligo can be used to isolate and/or immobilized the signal oligo. In any of the methods described herein utilizing a signal oligo, the signal oligo can be attached to an affinity tag.

Figure 7A:
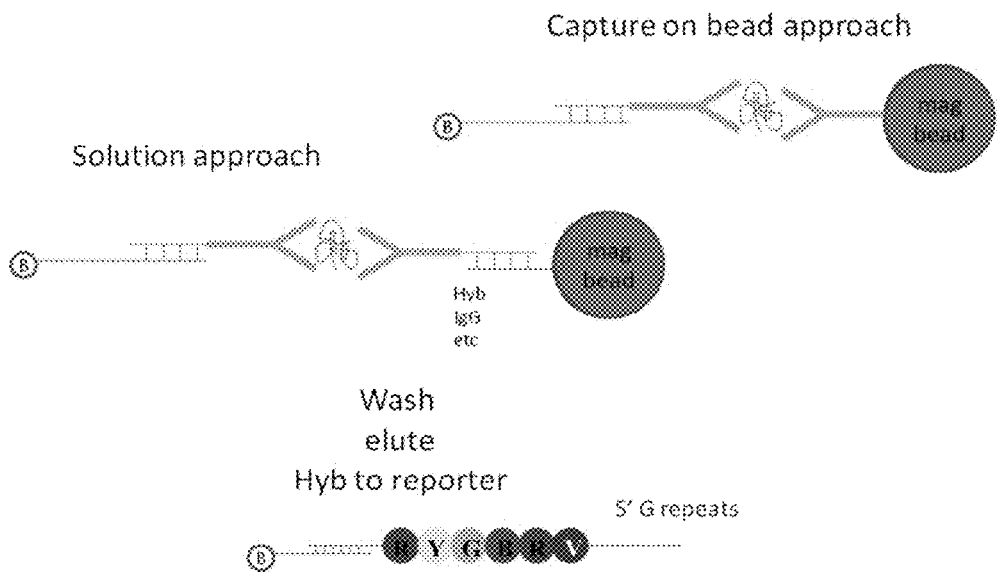
FIGS. 7A and 7B are schematic diagrams depicting an embodiment of the invention in which two antibodies specific for a target protein bind to the target protein in solution. The first antibody is a capture antibody, while the second antibody is attached to a partially double stranded nucleic acid probe, where one of the strands in the probe is attached to an affinity tag such as biotin. The binding of the first and second antibodies to the target protein formed a complex that can be isolated from the solution via the capture antibody. One of the strands of the partially double stranded nucleic acid probe can be eluted to generate a signal oligo containing the affinity tag. The signal oligo can then be hybridized to a nanoreporter to form a nanoreporter-signal oligo complex that can be isolated and/or immobilized into a solid surface. The nanoreporter-signal oligo complex can be analyzed by any the methods described herein. The label monomers of the nanoreporter (depicted as circles) emit individual signals of qualitatively different wavelengths that are spatially-distinguishable and are, from left to right positions, red (R), yellow (Y), green (G), blue (B), red (R), and violet (V).
Figure 7B:
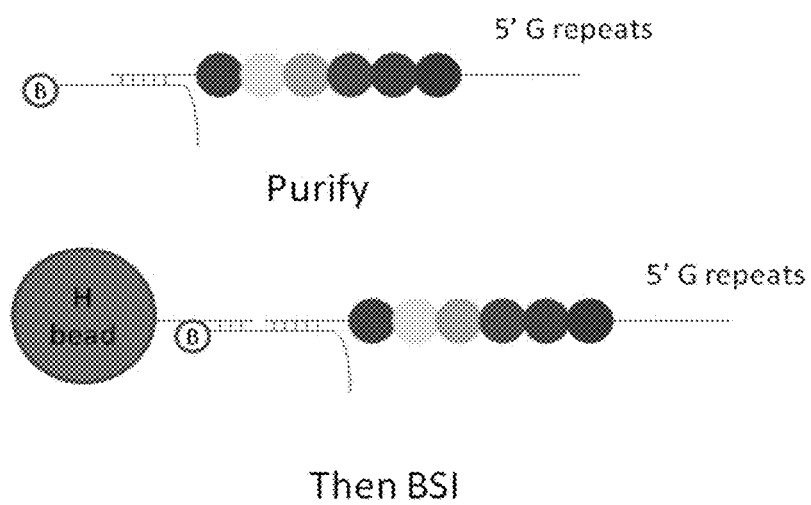

FIGS. 7A and 7B show schematic representations of one of the embodiments of the invention. This embodiment can be used with any of the methods described herein. The diagram in FIG. 7A shows antibodies as protein probes, however, this example can be used with any of the protein probes described herein. FIG. 7A shows an antibody attached directly or indirectly (e.g., via hybridization through an oligo) to a capture region (e.g., a magnetic bead) and a second antibody attached to a biotinylated signal oligo. However, the embodiment depicted in this figure can utilize any of the capture regions and affinity tags described herein. The target protein is mixed with the protein probes. The complex of target protein and antibodies is purified using the magnetic bead in the capture antibody. However, in this or any other embodiment described herein, the complex of target protein and protein probes can be purified by any suitable method known in art such as the methods described above. If the capture region is a slide or an array, the complex of target protein and protein probes can be purified by washing off the excess of unbound sample and protein probes. The isolated target protein/antibody complex is then washed and the signal oligo is eluted by any suitable method known in the art including those described herein. In the embodiment of FIG. 7B, the signal oligo is purified using oligonucleotide-coupled beads such as Dynabeads®. However, the signal oligo can be purified by any suitable method according to the affinity tag attached to it. The signal oligo is analyzed using nanoreporters as described below. In some embodiments, the methods depicted in FIGS. 7A and 7B are used to detect and/or quantify a plurality of target proteins. Each target protein will be detected by a probe set comprising a first probe and a second probe as described in FIG. 7A. Each probe set will have a specific and/or unique signal oligo that can then be associated to the target protein of each probe set. The embodiments described in FIGS. 7A and 7B provide the advantage that it requires only two bead purifications. In addition, in this embodiment, proteins and nanoreporters are largely separate, which eliminates concerns about protein stickiness.

In some embodiments, the signal oligo is generated by ligating two oligos that are in close proximity, e.g., proximity ligation. A diagram of proximity ligation is depicted in FIGS. 8A to 8D. In step 1) of FIG. 8A, probes containing the oligos are designed to bind pairwise to a target protein and to form a signal oligo by ligation when the probes are brought in proximity. FIGS. 8A to 8D show embodiments using antibodies as protein probes. However, the method described in FIGS. 8A to 8D can be used with any of the protein probes described herein. The probes containing the oligos can be prepared and purified by any methods known in the art, for example the methods described in Gullberg et al, PNAS 101(22), p 8420-24 (2004). In step 2) of FIG. 8A, the target protein is then mixed with the probes containing the oligos and the bridging oligos.

A bridging oligo comprises a polynucleotide sequence. The oligos attached to protein probes comprise a portion that is complementary to the bridging oligo. In some embodiments the complementary portions of the oligos are 5, 6, 7, 8, 9, 10, 11, 12, 13, 14, 15, 16, 17, 18, 19, 20, 21, 22, 23, 24, 25, 26, 27, 28, 29, 30, 40, 50, 60, 70 or more nucleotide bases. In some embodiments the complementary portions of the bridging oligo with each of the oligos attached to the protein probe are 6 to 15 bases, with a total length of bridging oligo is 12-30 bases. In some embodiments, the complementary portions of the oligos are 40 bases. In some embodiments, the complementary portions of the oligos are 30 bases. In some embodiments, the complementary portions of the oligos are 20 bases.

Figure 8A:
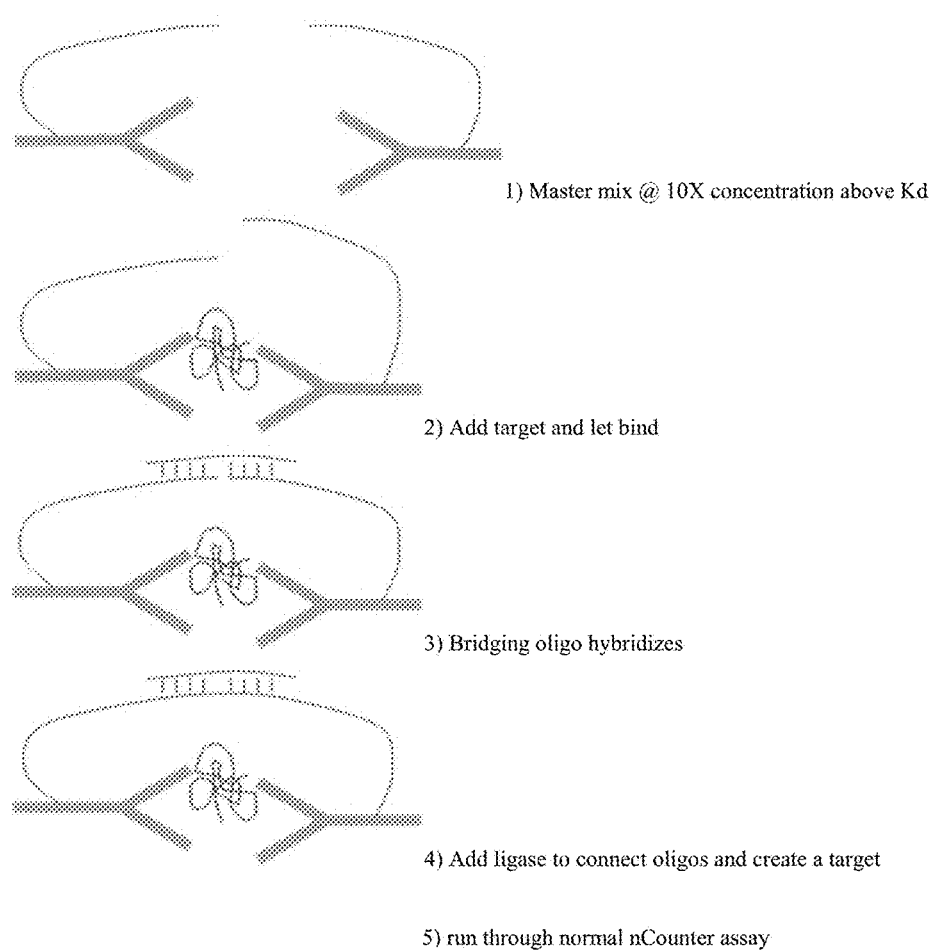
FIG. 8A is a schematic diagram depicting certain embodiments of the invention using proximity ligation. A first and a second oligo are attached to a first and a second antibody, respectively, both antibodies being specific for a target protein. The first and second antibodies bind to the target protein, bringing the first and second oligo to close proximity. A bridging oligo and a ligase are added to the solution to connect the first and second oligo to generate a signal oligo. The signal oligo can then be analyzed by any the methods described herein.

In step 4) of FIG. 8A, the components required for probe ligation are added. The oligos in the protein probes can be ligated by any suitable method known in art. Ligation according to the present invention comprises any enzymatic or chemical process wherein an inter-nucleotide linkage is formed between the opposing ends of nucleic acid sequences that are adjacently hybridized to the bridging oligo. Example of enzymes that can be used for ligation include but are not limited to DNA ligase, and RNA ligase such as T4 DNA ligase, T4 RNA ligase, *Thermus thermophilus* (Tth) ligase, *Thermus aquaticus* (Taq) DNA ligase, or *Pyrococcus furiosus* (Pfu) ligase. Chemical ligation can be performed using activating and reducing agents such as carbodiimide, cyanogen bromide (BrCN), imidazole, 1-methylimidazole/carbodiimide/cystamine, N-cyanoimidazole, dithiothreitol (DTT) and ultraviolet light. Also within the scope of the invention are ligation techniques such as gap-filling ligation, including, without limitation, gap-filling OLA and LCR, bridging oligonucleotide ligation, and correction ligation. Descriptions of these techniques can be found, among other places, in U.S. Pat. No. 5,185,243, published European Patent Applications EP 320308 and EP 439182, and PCT Publication Nos. WO 90/01069 and WO 01/57268.

Figure 8B:
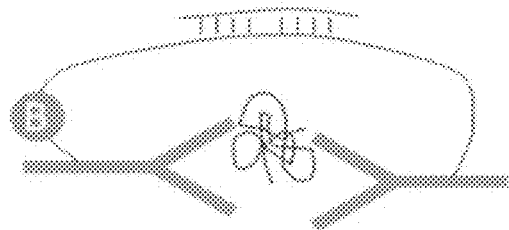
FIGS. 8B, 8C, and 8D are schematic diagrams depicting methods by which the signal oligo shown in FIG. 8A may be released and purified.
Figure 8C:
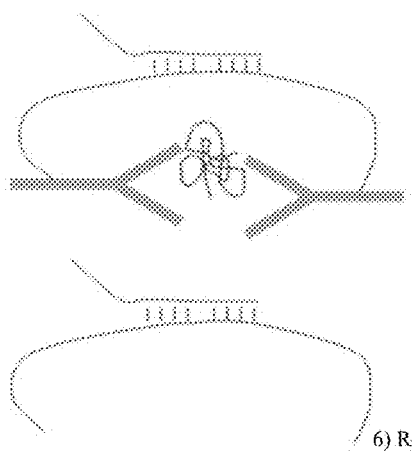
Figure 8D:
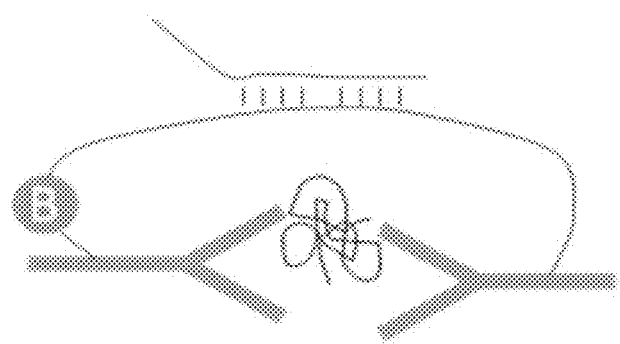

In step 5) of FIG. 8A, after ligation, the signal oligo is then released via disulfide reduction, uracil excision, restriction digest, proteinase K, or any other suitable method know in the art. Additionally, the signal oligo can be released by the methods depicted in FIGS. 8B to 8D. FIG. 8B, shows an embodiment in which the signal oligo has an affinity tag such as biotin or a sequence. The affinity tag can be used to isolate and/or immobilized the signal oligo as described herein. FIG. 8C shows an embodiment in which the bridging oligo has an affinity tag such as biotin or a sequence. The affinity tag can be used to isolate and/or immobilized the signal oligo as described herein. Only the ligated oligo will have enough overlap to remain hybridized to the signal oligo during the isolation and/or immobilization process. FIG. 8D shows an embodiment in which the embodiments of FIGS. 8B and 8C are combined. The signal oligo is analyzed using nanoreporters as described below. In some embodiments, the methods depicted in FIGS. 8A to 8D are used to detect and/or quantify a plurality of target proteins. Each target protein will be detected by a probe set comprising a first probe and a second probe as described in FIGS. 8A to 8D. Each probe set will have a specific and/or unique signal oligo that can then be associated to the target protein of each probe set. The embodiments described in FIGS. 8A to 8D have several benefits around sensitivity, minimization of cross-reactivity, and multiplexing. Proximity ligations have shown high sensitivity and have the effect of lowering the apparent Kd by essentially decreasing the off-rate.

In some embodiments utilizing proximity ligation one of the oligos is attached to a nanoreporter. FIG. 9 shows a diagram of one of such embodiments.

In step 1) of FIG. 9 probes containing the oligos are designed to bind pairwise to target proteins. One of the oligos in one of the protein probes is attached to a nanoreporter. FIG. 9 shows an embodiment using antibodies as protein probes. However, the method described in FIG. 9 can be used with any of the protein probes described herein. The probes containing the oligos can be prepared and purified as described above. In step 2) and 3) of FIG. 9, the target protein is then mixed with the probes containing the oligos and the bridging oligos. The bridging oligo binds to the oligo in a first protein probe and a portion of the nanoreporter attached to the second protein probe.

The oligo attached to the first protein probe and the nanoreporter comprise a portion that is complementary to the bridging oligo. In some embodiments the complementary portion is 5, 6, 7, 8, 9, 10, 11, 12, 13, 14, 15, 16, 17, 18, 19, 20, 21, 22, 23, 24, 25, 26, 27, 28, 29, 30, 40, 50, 60, 70 or more nucleotide bases. In some embodiments, the complementary portion is 40 bases. In some embodiments, the complementary portion is 30 bases. In some embodiments, the complementary portion is 20 bases. In some embodiments the complementary portions of the bridging oligo with each the oligos attached to the protein probe and the nanoreporter is 6 to 15 bases, with a total length of bridging oligo is 12-30 bases. In step 4) of FIG. 9, the components required for probe ligation are then added. The oligo in the first protein probe and the nanoreporter can be ligated by any suitable method known in art as described above. In step 5) of FIG. 9, after ligation, the signal oligo can be optionally released via disulfide reduction, uracil excision, restriction digest, proteinase K, or any other suitable method known in the art.

Figure 13:
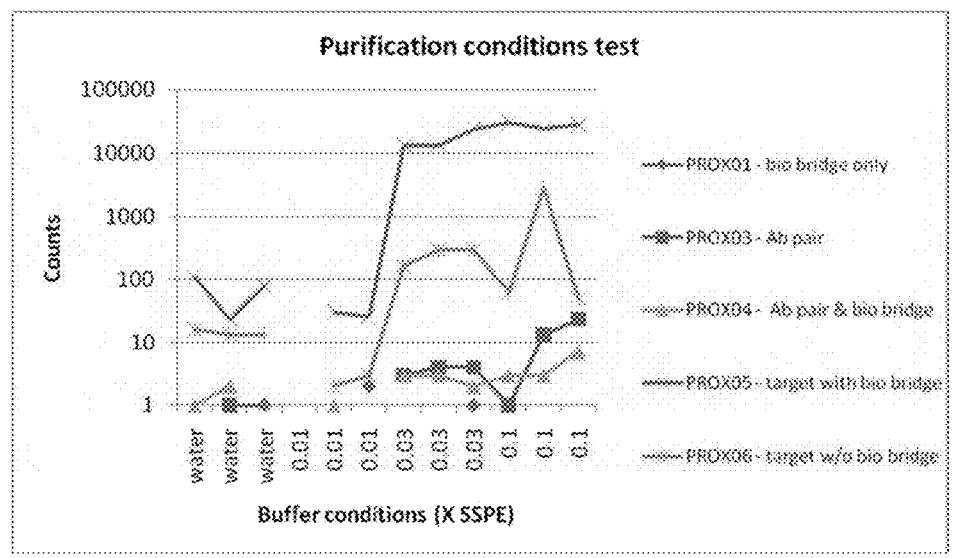
FIG. 13 is a graph depicting the total counts retained by various components of the antibody reporter complex (PROX01, PROX03, PROX04, PROX05, and PROX06) following purification and a rinsing step using either water or SSPE buffer of various fold concentrations (0.01×, 0.03×, or 0.1×). At 0.03×SSPE the oligo representing a ligated product, PROX05, was retained.

Additionally, the signal oligo can be released by the methods depicted in FIGS. 8B to 8D. For instance, using the approach described in FIG. 8C, a purification step is performed to separate ligated oligos from non-ligated oligos after release of the signal oligo from, for instance, an antibody. This purification step can be performed using magnetic beads or any other method known in the art for the physical separation of proteins. Importantly, if the amount of antibody used is higher than the amount of reporters used, then the resultant excess of unligated oligos may block the hybridization of the reporter to the oligo. As described in Example 7, the purification step further includes a rinsing step with a buffer solution. FIG. 13 demonstrates how various components of an antibody reporter complex are purified and rinsed in a variety of buffer conditions. A preferred rinsing buffer is SSPE; however, other buffers and all concentrations having similar capacities for retaining counts of a reporter complex or a component thereof are encompassed by these methods.

The signal oligo is analyzed using nanoreporters as described below. In some embodiments, the methods depicted in FIG. 9 are used to detect and/or quantify a plurality of target proteins. Each target protein will be detected by a probe set comprising a first probe and a second probe as described in FIG. 9. Each probe set will have a specific and/or unique signal oligo that can then be associated to the target protein of each probe set. The embodiments described in FIG. 9 take advantage of the decrease in the Koff via proximity ligation. A lower Koff means a lower Kd and the ability to work with lower concentrations of protein probe. This decrease in Kd makes it easier to work in concentrations required for reporters, and thus to contemplate direct detection approaches for multiplex analysis and lower reagent costs. These embodiments do not need a step for hybridization to reporters within the assay. Thus, these assays will be faster and have a shorter time to answer.

In some embodiments, the signal oligo is analyzed/detected using nanoreporter(s) as described in sections below. In these embodiments, the nanoreporter(s) comprise a portion that is complementary to the signal oligo. In some embodiments the complementary portion is 5, 6, 7, 8, 9, 10, 11, 12, 13, 14, 15, 16, 17, 18, 19, 20, 21, 22, 23, 24, 25, 26, 27, 28, 29, 30, 40, 50, 60, 70 or more nucleotide bases. In some embodiments, the complementary portion is 40 bases. In some embodiments, the complementary portion is 30 bases. In some embodiments, the complementary portion is 20 bases. In some embodiments, the complementary portion 15-20 bases.

In some embodiments, the methods described herein further comprise protein probes containing a nanoreporter. Thus, in some embodiments the invention provides methods for detection and/or quantification of a target protein by binding a protein probe or protein probe set to a target protein, wherein the protein probe or at least one of the protein probes in the probe set contains a nanoreporter.

Figure 4:
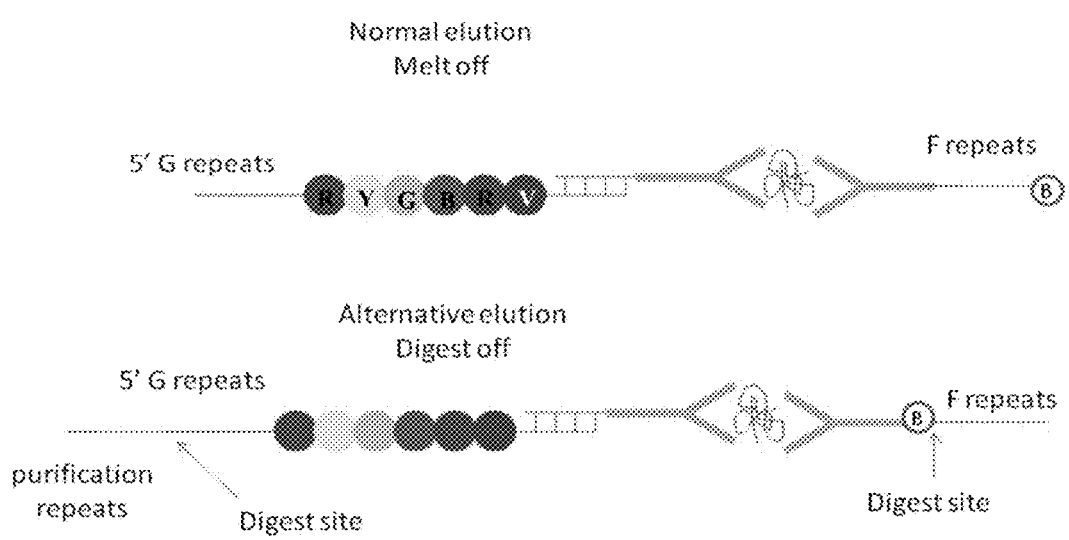
FIG. 4 is a schematic diagram depicting two alternate embodiments of the invention for solution tripartite binding. According to this method, two antibodies specific for a target protein bind to that target protein in solution. The first antibody is attached to an affinity tag such as biotin and contains a constant region, which, for example, contains F repeats. The second antibody is attached to a nanoreporter probe and a second constant region, which, for example, contains, G repeats. The binding of the first and second antibodies to the target protein forms a complex that can be isolated from the solution via the affinity tag of the first antibody. "Normal" elution of the complex is accomplished by melting off the G and F bead. "Alternative" elution of the complex is accomplished via digestion. The label monomers of the nanoreporter (depicted as circles) emit individual signals of qualitatively different wavelengths that are spatially-distinguishable and are, from left to right positions, red (R), yellow (Y), green (G), blue (B), red (R), and violet (V).

FIG. 4 shows a schematic diagram of one of the embodiments of the invention. In this embodiment a nanoreporter is attached to one of the antibodies. The methods described in FIG. 4 can be utilized using any of the protein probes described herein. In some embodiments, the nanoreporter can be directly attached to the protein probe. In other embodiments, the nanoreporter can be attached to a protein probe via hybridization through a linker oligo. Thus, the nanoreporter comprises a portion that is complementary to the linker oligo in the protein probe. In some embodiments the complementary portion is 5, 6, 7, 8, 9, 10, 11, 12, 13, 14, 15, 16, 17, 18, 19, 20, 21, 22, 23, 24, 25, 26, 27, 28, 29, 30, 40, 50, 60, 70 or more nucleotide bases. In some embodiments the linker oligo is 15-20 bases. In some embodiments, the complementary portion is 40 bases. In some embodiments, the complementary portion is 30 bases. In some embodiments, the complementary portion is 20 bases. In some embodiments, the complementary portion is 15 bases.

The hybridization of the nanoreporter to the linker oligo can occur at different temperatures depending of the length of the complementary portion. In some embodiments, the nanoreporter can be hybridized to a linker oligo attached to a protein probe at a temperature in the range of 32° C. to 40° C. In some embodiments, the nanoreporter can be hybridized to a linker oligo attached to a protein probe at a temperature of 35° C. In some embodiments, the nanoreporter can be hybridized to a linker oligo attached to a protein probe at a temperature of 37° C. In some embodiments, the nanoreporter can be hybridized to a linker oligo attached to a protein probe at a temperature of 45° C. In some embodiments, the nanoreporter can be hybridized to a linker oligo attached to a protein probe at a temperature of 52-57° C. In some embodiments, the nanoreporter can be hybridized to a linker oligo attached to a protein probe at a temperature of 15-20° C. below the melting temperature (Tm) of the complementary portions of the nanoreporter with the linker oligo. One of ordinary skilled in art will understand that the length of the complementary portions of the nanoreporter with the linker oligo and their hybridization temperature will depend on the type of protein probe used. In some embodiments, the protein probe is an antibody and the length of the complementary portions of the nanoreporter with the linker oligo is 15-20 bases, which gives a Tm of about 57° C. or 15-20° C. above the ideal antibody temperature of 37° C. Thus in some embodiments, the protein probe is an antibody, the length of the complementary portions of the nanoreporter with the linker oligo is 15-20 bases and the hybridizing temperature is 37° C.

FIG. 4 shows that a complex of target protein and antibodies is formed in which one of the antibodies is bound to biotin and the other antibody has a nanoreporter attached. The methods described in FIG. 4 can use any affinity tag described herein besides biotin. Purification of the target protein-antibodies complex can be performed by any suitable method known in the art including those described herein. Elution of the nanoreporter can be accomplished by melting off G and F beads, via digestion or any other suitable method known in the art. In the embodiments in which the protein-antibodies complex contain an affinity tag, the complex can be bound to a coverslip, e.g., coated with streptavidin (Optichem®, Accelr8 Technology Corporation). The nanoreporter is analyzed as described below. In some embodiments, the methods depicted in FIG. 4 are used to detect and/or quantify a plurality of target proteins. Each target protein will be detected by a probe set comprising a first probe and a second probe as described in FIG. 4. Each probe set will have a specific and/or unique nanoreporter that can then be associated to the target protein of each probe set.

Without intending to be limited to any theory or any specific embodiments, the embodiments of the inventions that utilize a signal oligo present several advantages: (1) these embodiments separate the target proteins and the protein probes from the nanoreporters. Separation of the proteins from the reporters eliminates the potential problems of solubility and stickiness associated with using nanoreporters to measure proteins. Separation of the target proteins from the nanoreporters avoids the Kd mismatch issues between DNA and proteins, allows for the use of ideal concentrations for both to get maximum signal and lowest noise, and allows for the use of low Kd antibodies if needed; (2) the indirect signal oligo approach can be run as a process upstream of the nanoreporter assay described below, thereby taking advantage of an optimized nanoreporter assay; (3) protein probe sets (e.g., antibody pairs) can be used in their normal configuration if needed, e.g., capture antibody on surface (on a magnetic bead for example), and detection antibody in solution. Some antibodies work best in this configuration; (4) with these embodiments problems associated with the protein probes coming off the target (Koff rate) are minimized, e.g., antibodies only have to stay bound to the target during binding and purification on the beads. This allows for use of a large range of antibodies including antibodies with lower binding affinity; and (5) proteins can be read in the same lane as nucleic acids, e.g., RNA or DNA. The sample is first split: part is run through the protein detection embodiments described herein (lyse cells with detergent then bind and purify as described herein), and part is split off and processed as nucleic acid samples (cells are lysed with GITC). The samples are then recombined and analyzed using nanoreporters as described below, potentially in the same lane. Measurement of both nucleic acids (e.g., RNA) and proteins in the same lane will minimize measurement differences, make protein and nucleic acid expression data more comparable, and eliminate the need for multiple measurement methods to get the required data.

In some embodiments, the methods described herein provide for the measurement of nucleic acids, e.g., RNA or DNA, in combination with the measurement of proteins.

Any of the embodiments described herein can be used in the detection of multiple target proteins. In some embodiments, the invention provides methods comprising protein probes for the analysis of target proteins. In some embodiments, the invention provides a protein probe population for use in a multiplexed assay. Each protein probe in the population is specific for a target molecule. The binding of the target proteins to the protein probes is then detected using nanoreporters. Each nanoreporter comprises a unique label code that can be associated to a specific target molecule as described below.

In some embodiments, the detection of the nanoreporters as described below is digital in nature in that one molecule at a time is counted. While fluorescence is used to read the code, the signals are high and the spot is either present of not, thus the digital detection. Using digital detection rather than an analogue fluorescent signal used to quantify signal leads to more accurate quantification. Thus the methods described herein allows for multiplexing to levels beyond currently possible, for more accurate quantification, and possibly higher sensitivity.

Nanoreporters

A nanoreporter which provides a code of signals (the nanoreporter label code) associated with a specific target. In some embodiments, upon binding of the nanoreporter to a signal oligo or a linker oligo associated with a protein probe, the nanoreporter code identifies the signal oligo or the protein probe to which the nanoreporter is bound. Thus, in some embodiments the nanoreporters of the invention comprise two main portions: (i) a sequence specific for a signal oligo-specific or a linker oligo associated with a protein probe; and (ii) a labeled nanoreporter. In some embodiments, the nanoreporters are directly attached to a protein probe.

Nanoreporters are modular structures. In some embodiments, the nanoreporter comprises a plurality of different detectable molecules. In some embodiments, a labeled nanoreporter is a molecular moiety containing certain basic elements: (i) a plurality of label attachment regions attached in linear combination, and (ii) complementary polynucleotide sequences attached to the label attachment regions of the backbone. In some embodiments, the labeled nanoreporter comprises 2, 3, 4, 5, 6, 7, 8, 9, 10 or more unique label attachment regions attached in a linear combination, and complementary polynucleotide sequences attached to the label attachment regions of the backbone. In some embodiments, the labeled nanoreporter comprises 3 or more label attachment regions attached in linear combination, and complementary polynucleotide sequences attached to the label attachment regions of the backbone. The term label attachment region includes a region of defined polynucleotide sequence within a given backbone that may serve as an individual attachment point for a detectable molecule.

The plurality of label attachment regions attached in linear combination can comprise uniquely designed sequences. In addition, the plurality of label attachment regions attached in linear combination in the nanoreporters can comprise at least one template, for example but not limited to, at least one nucleic acid sequence, such as at least part of a linear or linearizable viral genome, such as the genomes of adenovirus, hepatitis virus, herpes virus, rotavirus, and the like, or bacteriophages such as lambda, M13, φA-174, T-series bacteriophages, and the like, including derivatives thereof comprising cloning cassettes, polylinkers, and the like; plasmids, such as pBR322 and pUC series plasmids, etc., including derivatives thereof comprising cloning cassettes, polylinkers, and the like; synthetic templates; templates comprising artificial sequences; and the like. The skilled artisan will understand that virtually any piece of nucleic acid can serve as a template for fabricating a nanoreporter provided that it is large enough to include at least two label attachment regions, or it can be combined with at least one other nucleic acid sequence so that the combined sequence is large enough to include at least two label attachment regions.

In some embodiments, the labeled nanoreporter also comprises a backbone containing a constant region. The constant region can be directly or indirectly attached to the nanoreporter. Thus, the constant region can covalently attached to a nanoreporter or the constant region can be bound to the nanoreporter later in the assay. The term constant region includes tandemly-repeated sequences of about 10 to about 25 nucleotides. The constant region can be attached at either the 5' region or the 3' region of a nanoreporter, and may be utilized for capture and immobilization of a nanoreporter for imaging or detection, such as by attaching to a solid substrate a sequence that is complementary to the constant region.

The elements of a nanoreporter can be found in a single molecular moiety (a singular nanoreporter), or two distinct molecular moieties (a dual nanoreporter). Each molecular moiety may be composed of one molecule or more than one molecule attached to one another by covalent or non-covalent means. In some embodiments, each component of a dual nanoreporter has a signal oligo-specific sequence that binds to a different site on the same signal oligo molecule. When using a dual nanoreporter system one of the nanoreporter probes may be unlabeled. In some embodiments, the unlabeled nanoreporter probe may comprise a capture region. In some embodiments, the unlabeled nanoreporter probe may comprise a signal oligo-specific region and a backbone that may be single stranded. In some embodiments, the unlabeled nanoreporter probe may comprise a signal oligo-specific region and a backbone that may be double stranded.

The complementary polynucleotide sequences attached to a nanoreporter backbone serve to attach detectable molecules, or label monomers, to the nanoreporter backbone.

The complementary polynucleotide sequences may be directly labeled, for example, by covalent incorporation of one or more detectable molecules into the complementary polynucleotide sequence. Alternatively, the complementary polynucleotide sequences may be indirectly labeled, such as by incorporation of biotin or other molecule capable of a specific ligand interaction into the complementary polynucleotide sequence. In such instances, the ligand (e.g., streptavidin in the case of biotin incorporation into the complementary polynucleotide sequence) may be covalently attached to the detectable molecule. Where the detectable molecules attached to a label attachment region are not directly incorporated into the complementary polynucleotide sequence, this sequence serves as a bridge between the detectable molecule and the label attachment region, and may be referred to as a bridging molecule, e.g., a bridging nucleic acid.

In some embodiments, the invention uses the nanoreporters described in U.S. Pat. No. 7,473,767; U.S. application Ser. Nos. 10/542,458; 12/324,357; 11/645,270 and 12/541,131, incorporated herein by reference in their entireties.

The nucleic-acid based nanoreporter, nanoreporter-signal oligo complexes, or nanoreporter-protein probe complexes of the present invention comprise nucleic acids, which may be affinity-purified or immobilized using a nucleic acid, such as an oligonucleotide, that is complementary to the constant region of the nanoreporter. As noted above, in some embodiments the nanoreporters comprise at least one constant region, which may serve as an affinity tag for purification and/or for immobilization (for example to a solid surface). The constant region typically comprises two or more tandemly-repeated regions of repeat nucleotides, such as a series of 15-base repeats. In such exemplary embodiments, the nanoreporter, whether complexed to a signal oligo, a target molecule or otherwise, can be purified or immobilized by an affinity reagent coated with a 15-base oligonucleotide which is the reverse complement of the repeat unit.

Nanoreporters, nanoreporter-signal oligo complexes, or nanoreporter-protein probe complexes can be purified in two or more affinity selection steps. For example, in the embodiments in which the nanoreporter is attached to a protein probe, the nanoreporter can comprise an affinity tag. In other embodiments when a signal oligo and dual nanoreporters are used, one nanoreporter probe can comprise a first affinity tag and the other nanoreporter probe can comprise a second (different) affinity tag. The nanoreporter probes are mixed with the signal oligos, and complexes comprising the two probes of the dual nanoreporters are separated from unbound materials (e.g., the signal oligo or the individual probes of the nanoreporter) by affinity purification against one or both individual affinity tags. In the first step, the mixture can be bound to an affinity reagent for the first affinity tag, so that only probes comprising the first affinity tag and the desired complexes are purified. The bound materials are released from the first affinity reagent and optionally bound to an affinity reagent for the second affinity tag, allowing the separation of complexes from nanoreporter probes comprising the first affinity tag. At this point only full complexes would be bound. The complexes are finally released from the affinity reagent for the second affinity tag and then preferably stretched and imaged. The affinity reagent can be any solid surface coated with a binding partner for the affinity tag, such as a column, bead (e.g., latex or magnetic bead) or slide coated with the binding partner. Immobilizing and stretching nanoreporters using affinity reagents is fully described in U.S. Provisional Application No. 60/753,816 by Sean M. Ferree and Dwayne L. Dunaway, entitled "Compositions Comprising Oriented, Immobilized Macromolecules and Methods for Their Preparation," filed on Dec. 23, 2005, and U.S. Pat. No. 7,473,767; U.S. application Ser. Nos. 10/542,458; 12/324,357; 11/645,270 and 12/541,131, incorporated herein by reference in their entirety.

The sequence of signals provided by the label monomers associated with the various label attachment regions of the backbone of a given nanoreporter allows for the unique identification of the nanoreporter. For example, when using fluorescent labels, a nanoreporter having a unique identity or unique spectral signature is associated with a signal oligo-specific sequence or a protein probe that recognizes a specific target molecule or a portion thereof. Detection of the nanoreporter signal, such as the spectral code of a fluorescently labeled nanoreporter, associated with the nanoreporter allows detection of the presence of the target molecule in the mixture (qualitative analysis). Counting all the label monomers associated with a given spectral code or signature allows the counting of all the molecules in the mixture associated with the signal oligo-specific sequence or the protein probe coupled to the nanoreporter (quantitative analysis). In the embodiments where a signal oligo is used, the signal oligos then can be correlated to the target molecule via the binding of target molecule to the protein probe associated with the signal oligo. Nanoreporters are thus useful for the diagnosis or prognosis of different biological states (e.g., disease vs. healthy) by quantitative analysis of known biological markers.

Moreover, the exquisite sensitivity of single molecule detection and quantification provided by the nanoreporters of the invention allows for the identification of new diagnostic and prognostic markers, including those whose fluctuations among the different biological states is too slight detect a correlation with a particular biological state using traditional molecular methods. The sensitivity of nanoreporter-based molecular detection permits detailed pharmacokinetic analysis of therapeutic and diagnostic agents in small biological samples.

Nanoreporters' syntheses can be performed by any suitable methods known in the art. Examples of nanoreporters' syntheses are described in U.S. Pat. No. 7,473,767; U.S. application Ser. Nos. 10/542,458; 12/324,357; 11/645,270 and 12/541,131, incorporated herein by reference in their entireties.

In one embodiment, the invention provides a nanoreporter further comprising an affinity tag attached to the nanoreporter backbone, such that attachment of the affinity tag to a support allows backbone stretching and resolution of signals provided by label monomers corresponding to different label attachment regions on the backbone. Nanoreporter stretching may involve any stretching means known in the art including but not limited to, means involving physical, hydrodynamic or electrical means. The affinity tag may comprise a constant region.

The uniqueness of each nanoreporter probe in a population of probe allows for the multiplexed analysis of a plurality of target molecules. For example, in some embodiments, each nanoreporter probe can contain contains six label attachment regions, where each label attachment region of each backbone is different from the other label attachment regions in that same backbone. If the label attachment regions are going to be labeled with one of four colors and there are 24 possible unique sequences for the label attachment regions and each label attachment region is assigned a specific color, each label attachment region in each backbone will consist of one of four sequences. There will be 4096 possible nanoreporters in this example. The number of possible nanoreporters can be increased, for example, by increasing the number of colors, increasing the number of unique sequences for the label attachment regions and/or increasing the number of label attachment regions per backbone. Likewise the number of possible nanoreporters can be decreased by decreasing the number of colors, decreasing the number of unique sequences for the label attachment regions and/or decreasing the number of label attachment regions per backbone.

In certain embodiments, the methods of detection are performed in multiplex assays, whereby a plurality of target molecules is detected in the same assay (a single reaction mixture). In a preferred embodiment, the assay is a hybridization assay in which the plurality of target molecules is detected simultaneously. In certain embodiments, the plurality of target molecules detected in the same assay is, at least 2, at least 5 different target molecules, at least 10 different target molecules, at least 20 different target molecules, at least 50 different target molecules, at least 75 different target molecules, at least 100 different target molecules, at least 200 different target molecules, at least 500 different target molecules, or at least 750 different target molecules, or at least 1000 different target molecules. In other embodiments, the plurality of target molecules detected in the same assay is up to 50 different target molecules, up to 100 different target molecules, up to 150 different target molecules, up to 200 different target molecules, up to 300 different target molecules, up to 500 different target molecules, up to 750 different target molecules, up to 1000 different target molecules, up to 2000 target molecules, or up to 5000 target molecules. In yet other embodiments, the plurality of target molecules detected is any range in between the foregoing numbers of different target molecules, such as, but not limited to, from 20 to 50 different target molecules, from 50 to 200 different target molecules, from 100 to 1000 different target molecules, from 500 to 5000 different target molecules, and so on and so forth.

In addition to the qualitative analytical capabilities provided by the nanoreporters of the invention and the analytical techniques based thereon, the nanoreporters of the invention are uniquely suitable for conducting quantitative analyses. By providing a one to one binding between the nanoreporters (whether singular or dual nanoreporters) of the invention and their target molecules in a biomolecular sample, all or a representative portion of the target molecules present in the sample can be identified and counted. This individual counting of the various molecular species provides an accurate and direct method for determining the absolute or relative concentration of the target molecule in the biomolecular sample. Moreover, the ability to address each molecule in a mixture individually leverages benefits of miniaturization including high sensitivity, minimal sample quantity requirements, high reaction rates which are afforded by solution phase kinetics in a small volume, and ultimately very low reagent costs.

Detectable Molecules or Label Monomers

The nanoreporters of the present invention can be labeled with any of a variety of label monomers, such as a radioisotope, fluorochrome, dye, enzyme, nanoparticle, chemiluminescent marker, biotin, or other monomer known in the art that can be detected directly (e.g., by light emission) or indirectly (e.g., by binding of a fluorescently-labeled antibody). Generally, one or more of the label attachment regions in the nanoreporter is labeled with one or more label monomers, and the signals provided by the label monomers attached to the label attachment regions of a nanoreporter constitute a detectable code that identifies the target to which the target-specific region of the nanoreporter binds. In certain embodiments, the lack of a given signal from the label attachment region (e.g., a dark spot) can also constitute part of the nanoreporter code.

Example of label monomers that can be used with the nanoreporters described herein and methods to incorporate the labels monomers into the nanoreporters are described in U.S. Pat. No. 7,473,767; U.S. application Ser. Nos. 10/542,458; 12/324,357; 11/645,270 and 12/541,131, incorporated herein by reference in their entireties.

Affinity Tags

A variety of affinity tags known in the art may be used, e.g., to purify and/or immobilize nanoreporters. In some embodiments, a biotin anchor is attached to the nanoreporter, allowing immobilization of the nanoreporter on a streptavidin coated slide.

In some embodiments, a labeled nanoreporter will contain an affinity tag at each end, A1 and A2. The labeled nanoreporter can be immobilized to a surface through the binding of A1 to an immobilized affinity partner. In the absence of an affinity binding partner for A2, the A2 end of the nanoreporter remains in solution, but in the presence of an affinity binding partner (A2'), the A2 end of the nanoreporter is also immobilized. In some embodiments, a labeled nanoreporter will contain a single affinity tag, A1. Another affinity tag, A2, can be attached to the nanoreporter by direct binding of the nanoreporter to a molecule containing A2 (e.g., if the nanoreporter is or comprises a nucleic acid, it can hybridize directly with another nucleic acid to which A2 is attached). Alternatively, either affinity tag can be attached to the labeled nanoreporter via a bridging molecule, such as the bridging nucleic acid. In some embodiments, upon immobilization of A1, the nanoreporter can be stretched, or "elongated", for example by electrostretching, for separation of the label attachment regions in a manner that permits detection of the nanoreporter code. Optionally, while the nanoreporter is in an elongated state, A2 is introduced and binds the end of the nanoreporter that is complementary to A2 down to the surface.

In some embodiments, an affinity tag is attached to a protein probe, e.g., to purify and/or immobilize the protein probe.

An affinity tag can be used for attachment to beads or other matrixes for a variety of useful applications including but not limited to purification.

Examples of affinity tags and methods of making and/or attaching them to the nanoreporters described herein are described in U.S. Pat. No. 7,473,767; U.S. application Ser. Nos. 10/542,458; 12/324,357; 11/645,270 and 12/541,131, incorporated herein by reference in their entireties.

Biomolecular Samples

The protein probe and nanoreporter systems of the invention can be used to detect target proteins in any biomolecular sample. As will be appreciated by those in the art, the sample may comprise any number of things, including, but not limited to: biological samples, such as cells (including both primary cells and cultured cell lines), cell lysates, or extracts, tissues and tissue extracts; bodily fluids (including, but not limited to, blood, urine, serum, lymph, bile, cerebrospinal fluid, interstitial fluid, aqueous or vitreous humor, colostrum, sputum, amniotic fluid, saliva, anal and vaginal secretions, perspiration and semen, a transudate, an exudate (e.g., fluid obtained from an abscess or any other site of infection or inflammation) or fluid obtained from a joint (e.g., a normal joint or a joint affected by disease such as rheumatoid arthritis, osteoarthritis, gout or septic arthritis) of virtually any organism, with mammalian samples being preferred and human samples being particularly preferred; environmental samples (including, but not limited to, air, agricultural, water and soil samples); biological warfare agent samples; research samples including extracellular fluids, extracellular supernatants from cell cultures, inclusion bodies in bacteria, cellular compartments, cellular periplasm, mitochondria compartment, etc.

The biomolecular samples can be indirectly derived from biological specimens. For example, where the target protein of interest is a kinase the biomolecular sample of the invention can be a sample containing isolated proteins from a cell lysate. In another example, the biomolecular sample of the invention is generated by subjecting a biological specimen to fractionation, e.g., size fractionation or membrane fractionation.

The biomolecular samples of the invention may be either native, e.g., not subject to manipulation or treatment, or treated, which can include any number of treatments, including exposure to candidate agents including drugs, genetic engineering (e.g., the addition or deletion of a gene), etc.

Biomolecular samples may also include environmental samples, such as those containing bacteria or other organisms, such as diatoms, dinoflagellates, algae, among others, such as in certain marine or earth-based samples.

Detection of Nanoreporters

Nanoreporters are detected by any means available in the art that is capable of detecting the specific signals on a given nanoreporter. Where the nanoreporter is fluorescently labeled, suitable consideration of appropriate excitation sources may be investigated. Possible sources may include but are not limited to arc lamp, xenon lamp, lasers, light emitting diodes or some combination thereof. The appropriate excitation source is used in conjunction with an appropriate optical detection system, for example an inverted fluorescent microscope, an epi-fluorescent microscope or a confocal microscope. Preferably, a microscope is used that can allow for detection with enough spatial resolution to determine the sequence of the spots on the nanoreporter. For example in one embodiment an image of a dual nanoreporter hybridized to a target molecule can be obtained. If for example, the nanoreporters are labeled with three different colors, Alexa 488, Cy3 and Alexa 647 (labeled 1, 2 and 3, respectively). Colors 1, 2 and 3 are each acquired in different channels and the first and second registers, which can be seen as rows of spots, are shifted up by several pixels to be able to show each register individually.

Examples of methods for detection of nanoreporters that can be used in the methods of the invention are described in U.S. Pat. No. 7,473,767 entitled "Methods for detection and quantification of analytes in complex mixtures", US patent publication no. 2007/0166708 entitled "Methods for detection and quantification of analytes in complex mixtures", U.S. application Ser. No. 11/645,270 entitled "Compositions comprising oriented, immobilized macromolecules and methods for their preparation", PCT application no U.S. Ser. No. 06/049,274 entitled "Nanoreporters and methods of manufacturing and use thereof", and U.S. provisional application 60/088,988 entitled "Stable nanoreporter", all of which are incorporated by reference herein in its entirety.

Applications for Protein Detection Via Nanoreporter Technology

The compositions and methods of the invention can be used for diagnostic, prognostic, therapeutic, patient stratification, drug development, treatment selection and screening purposes. The present invention provides the advantage that many different target proteins can be analyzed at one time from a single biomolecular sample using the methods of the invention. This allows, for example, for several diagnostic tests to be performed on one sample.

The composition and methods of the invention can be used in proteomics. The methods described herein will typically provide an answer rapidly which is very desirable for this application. The methods and composition described herein can be used in the process of finding biomarkers that may be used for diagnostics or prognostics and as indicators of health and disease. The methods and composition described herein can be used to screen for drugs, e.g., drug development, selection of treatment, determination of treatment efficacy and/or identify targets for pharmaceutical development. The ability to test protein expression on screening assays involving drugs is very important because proteins are the final gene product in the body. In some embodiments, the methods and compositions described herein will measure both protein and gene expression simultaneously which will provide the most information regarding the particular screening being performed.

The present methods can be applied to the analysis of biomolecular samples obtained or derived from a patient so as to determine whether a diseased cell type is present in the sample, the stage of the disease, the prognosis for the patient, the ability to the patient to respond to a particular treatment, or the best treatment for the patient. The present methods can also be applied to identified biomarkers for a particular disease In some embodiments, the methods described herein are used in the diagnosis of a condition. As used herein the term "diagnose" or "diagnosis" of a condition includes predicting or diagnosing the condition, determining predisposition to the condition, monitoring treatment of the condition, diagnosing a therapeutic response of the disease, and prognosis of the condition, condition progression, and response to particular treatment of the condition. For example, a blood sample can be assayed according to any of the methods described herein to determine the presence and/or quantity of markers of a disease or malignant cell type in the sample, thereby diagnosing or staging the a disease or a cancer.

In some embodiments, the methods and composition described herein are used for the diagnosis and prognosis of a condition.

Numerous immunologic, proliferative and malignant diseases and disorders are especially amenable to the methods described herein. Immunologic diseases and disorders include allergic diseases and disorders, disorders of immune function, and autoimmune diseases and conditions. Allergic diseases and disorders include but are not limited to allergic rhinitis, allergic conjunctivitis, allergic asthma, atopic eczema, atopic dermatitis, and food allergy. Immunodeficiencies include but are not limited to severe combined immunodeficiency (SCID), hypereosinophilic syndrome, chronic granulomatous disease, leukocyte adhesion deficiency I and II, hyper IgE syndrome, Chediak Higashi, neutrophilias, neutropenias, aplasias, Agammaglobulinemia, hyper-IgM syndromes, DiGeorge/Velocardial-facial syndromes and Interferon gamma-TH1 pathway defects. Autoimmune and immune dysregulation disorders include but are not limited to rheumatoid arthritis, diabetes, systemic lupus erythematosus, Graves' disease, Graves ophthalmopathy, Crohn's disease, multiple sclerosis, psoriasis, systemic sclerosis, goiter and struma lymphomatosa (Hashimoto's thyroiditis, lymphadenoid goiter), alopecia aerata, autoimmune myocarditis, lichen sclerosis, autoimmune uveitis, Addison's disease, atrophic gastritis, myasthenia gravis, idiopathic thrombocytopenic purpura, hemolytic anemia, primary biliary cirrhosis, Wegener's granulomatosis, polyarteritis nodosa, and inflammatory bowel disease, allograft rejection and tissue destructive from allergic reactions to infectious microorganisms or to environmental antigens.

Proliferative diseases and disorders that may be evaluated by the methods of the invention include, but are not limited to, hemangiomatosis in newborns; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Duputren's fibrosis, cirrhosis, atherosclerosis and vascular restenosis.

Malignant diseases and disorders that may be evaluated by the methods of the invention include both hematologic malignancies and solid tumors.

Hematologic malignancies are especially amenable to the methods of the invention when the sample is a blood sample, because such malignancies involve changes in blood-borne cells. Such malignancies include non-Hodgkin's lymphoma, Hodgkin's lymphoma, non-B cell lymphomas, and other lymphomas, acute or chronic leukemias, polycythemias, thrombocythemias, multiple myeloma, myelodysplastic disorders, myeloproliferative disorders, myelofibroses, atypical immune lymphoproliferations and plasma cell disorders.

Plasma cell disorders that may be evaluated by the methods of the invention include multiple myeloma, amyloidosis and Waldenstrom's macroglobulinemia.

Example of solid tumors include, but are not limited to, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

The methods described herein can be used to diagnose pathogen infections, for example infections by intracellular bacteria and viruses, by determining the presence and/or quantity of markers of bacterium or virus, respectively, in the sample.

A wide variety of infectious diseases can be detected by the process of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia, B-Hemolytic strep., Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia,* and *Acitnomycetes.*

Fungal infectious agents which can be detected by the present invention include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis,* and *Maduromycosis.*

Viral infectious agents which can be detected by the present invention include human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present invention include *Plasmodium falciparum, Plasmodium malaria, Plasmodium vivax, Plasmodium ovale, Onchoverva volvulus, Leishmania, Trypanosoma* spp.*, Schistosoma* spp.*, Entamoeba histolytica, Cryptosporidum, Giardia* spp.*, Trichimonas* spp.*, Balatidium coli, Wuchereria bancrofti, Toxoplasma* spp.*, Enterobius vermicularis, Ascaris lumbricoides, Trichuris trichiura, Dracunculus medinesis, trematodes, Diphyllobothrium latum, Taenia* spp.*, Pneumocystis carinii,* and *Necator americanis.*

The present invention is also useful for detection of drug resistance by infectious agents. For example, vancomycin-resistant *Enterococcus faecium,* methicillin-resistant *Staphylococcus aureus,* penicillin-resistant *Streptococcus pneumoniae,* multi-drug resistant *Mycobacterium tuberculosis,* and AZT-resistant human immunodeficiency virus can all be identified with the present invention Thus, the target molecules detected using the compositions and methods of the invention can be either patient markers (such as a cancer marker) or markers of infection with a foreign agent, such as bacterial or viral markers.

Because of the quantitative nature of nanoreporters, the compositions and methods of the invention can be used to quantitate target protein whose abundance is indicative of a biological state or disease condition, for example, blood markers that are upregulated or downregulated as a result of a disease state.

In some embodiments, the methods and compositions of the present invention can be used for cytokine detection. The low sensitivity of the methods described herein would be helpful for early detection of cytokines, e.g., as biomarkers of a condition, diagnosis or prognosis of a disease such as cancer, and the identification of subclinical conditions.

Kits

The invention further provides kits comprising one or more components of the invention. The kits can comprise, for example, one or more protein probe sets and/or one or more nanoreporters. The kits can be used for any purpose apparent to those of skill in the art, including those described above.

In certain embodiments, the present invention also provides kits useful for the extension and selective immobilization of nanoreporters. The kits can comprise a substrate for immobilization and one or more binding partners to facilitate extension or immobilization of a nanoreporter. The binding partners could, in certain embodiments, comprise a moiety useful for extension of the nanoreporter in an appropriate force. In certain embodiments, the binding partners could facilitate immobilization or selective immobilization of the nanoreporter to the surface. In further embodiments, the kits could comprise a nanoreporter for extension and immobilization. In further embodiments, the kits could comprise a device capable of extending the nanoreporter.

The kits can contain a population of protein probes and/or nanoreporters as described herein.

The kits can contain pre-labeled nanoreporters, or unlabeled nanoreporters with one or more components for labeling the nanoreporters. Moreover, the nanoreporters provided in a kit may or may not have target-specific sequences pre-attached. In one embodiment, the target sequences are provided in the kit unattached to the nanoreporter backbone.

The kits can comprise other reagents such as signal oligos, linker oligos and bridging oligos. In some embodiments, the kits can separate the protein probe pairs into different premixes.

The kits can include other reagents as well, for example, buffers for performing hybridization reactions, linkers, restriction endonucleases, and DNA I ligases.

The kits also will include instructions for using the components of the kit, and/or for making and/or using the labeled nanoreporters.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1. Detection of Proteins Using Indirect Measurements—Sandwich Assay in Solution A diagram of the protocol for this Example is depicted in FIG. 1. In this Example the assay is set up to separate the binding of the protein target from the hybridization of the reporters to eliminate issues with the mismatch between low binding affinity of protein probes and the working concentration of reporters.

Label of Detection Antibody with Oligo and Purification

The linker oligos were attached to the antibody by random amine attachment using a 10 to 1 ratio of linker oligos to antibodies. Briefly, bifunctional crosslinker Sulfosuccinimidyl 4-[p-maleimidophenyl]butyrate (SMPB) (Thermo-Fisher, Inc., Waltham, Mass.) was coupled to anti-IL2 antibody A then reacted to thiolated oligo to crosslinker at an antibody:oligo ratio of 1:3 at room temperature. The antibody A linked to SMPB was purified by running the mixture thru Zeba column 2×, 1000G, (ThermoFisher, Inc., Waltham, Mass.) and the yield is determined.

To couple oligo to SMPB linked IL-2 antibody A the oligo was added to purified antibody linked to SMPB at 4° C.

The oligo linked to IL-2 antibody A the antibody-SMPB-oligo and PBE were added to Pall Nanosep® Centrifugal Device with Omega Membrane, (MWCO 100 kDa, Sigma-Aldrich, Inc., St. Louis, Mo.) was washed and centrifuged.

Hybridization of Signal Oligo to Detection Antibody

The signal oligo was preannealed to the oligo linked to IL-2 antibody A by adding oligo linked Il2 antibody A and signal oligo in a ratio of 3:2, signal oligo:Antibody ratio Other ratios are contemplated.

Formation of Target and Antibodies Complex

IL-2 antibody A annealed to signal oligo was mixed with biotinylated antibody B (BAF202, R&D systems, Inc., Minneapolis, Minn.) at approximately $1\times10^{-15}$ to $1\times10^{-8}$ M, and blockers (salmon sperm), with room to add target solution. The target protein IL-2 was added to the desired dilution ($<1\times10^{-8}$M). Antibodies were at 10× concentration over an estimated Kd of $10^{0-15}$ to $10^{0-8}$ M. The mixture was incubated.

The complex of target protein and antibodies was purified using Streptavidin-coupled Dynabeads® (Invitrogen) according to protocol.

Elution of Signal Oligo

The isolated target protein/antibody complex was washed and the signal oligo was eluted at greater than 45° C. using 0.1×SSPE for 10 to 15 minutes. Shorter and longer periods are contemplated Detection of Signal Oligo Detection of the signal oligo in each sample was carried out using a dual nanoreporter system having both labeled nanoreporter probes and unlabeled nanoreporter probes. The signal oligos from each sample were hybridized with final concentrations of the hybridization reagents as follows: unlabeled, biotinylated probe labeled reporter probe, 5×SSPE (pH 7.5), 5×Denhardt's reagent (Sigma), sheared salmon sperm DNA (Sigma), and detergent. Reagents were mixed and incubated in a thermocycler block with a heated lid for 16 hours.

Post-Hybridization Purification

To remove unhybridized reporters, reactions were purified over magnetic beads (Invitrogen™) coupled to oligonucleotides complementary to the 3'-repeat sequence contained on every biotinylated probe. Reactions were first diluted SSPE in 0.1% detergent mixture/TE and allowed to bind to beads at greater than 20° C. with continuous rotation. The beads were washed three times in SSPE and detergent and the hybridized complexes eluted in of 0.1×SSPE/0.1%/detergent mixture for 15 minutes at 45° C. After elution, samples were purified a second time to remove excess biotinylated probes by binding to magnetic beads coupled to oligonucleotides complementary to the 5'-repeat sequence contained on every reporter probe. The elutions from the anti-3'-repeat beads were brought to a final concentration of 1×SSPE and bound for 15 minutes at 22.5° C. with rotation. Beads were washed as above and eluted in of 0.1×SSPE/0.1%/detergent mixture at greater than 40° C. The doubly-purified samples were then prepared for capture as described below.

NanoString Reporter Capture, Stretching, and Imaging

Figure 2:
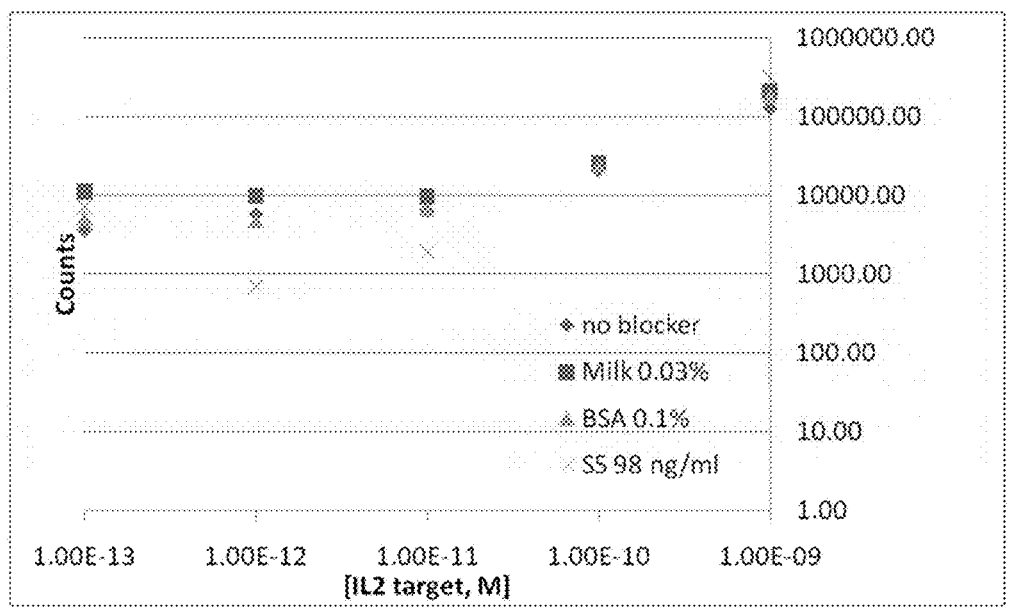
FIG. 2 is a graph depicting the results of a detection assay using the IL-2 target protein at different concentrations. Specifically, the detection of IL-2 within solutions containing no blocker, milk at 0.03%, bovine serum albumin (BSA) at 0.1%, or salmon sperm (SS) at 98 ng/ml, was measured as the total counts detected as a function of increasing IL-2 target protein molar concentration ([IL2 target, M]).
Figure 3:
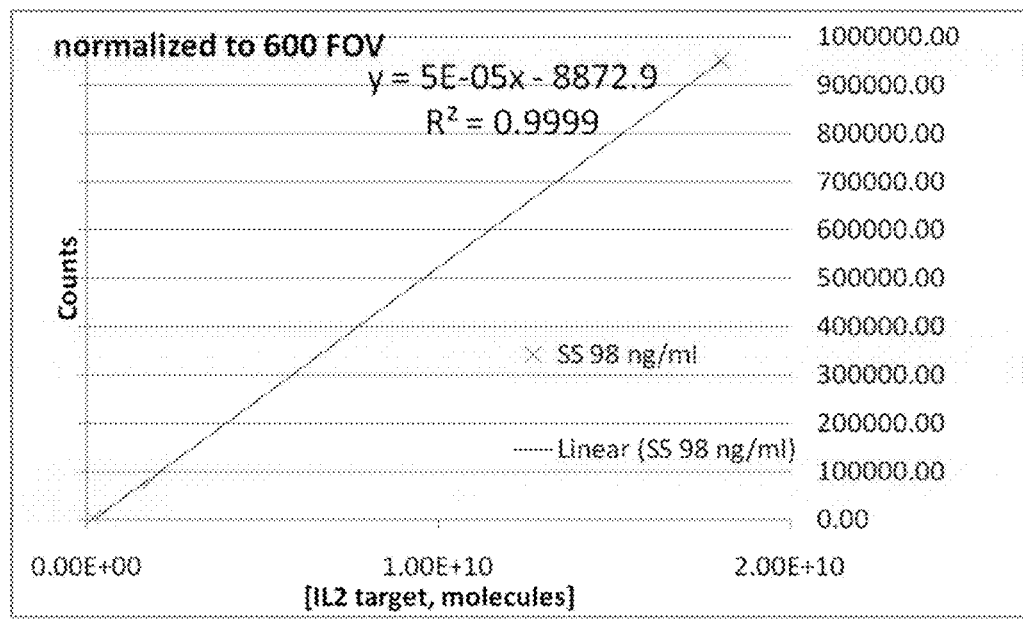
FIG. 3 is a graph depicting the efficiency of IL-2 detection in the assay used in FIG. 2. Total counts detected were normalized to 600 molecules per field of view (FOV) and expressed as a function of increasing concentration of IL2 target protein molecules ([IL2 target, molecules]). The efficiency of detection is the slope of the line depicted in this graph.

A solution of a custom-formulation of Tetraspeck fluorescent microspheres (Invitrogen™) was added to each sample. Samples were loaded into a NanoString fluidic device processed and imaged. Results:

Results are shown in FIG. 2. The results of this experiment showed that IL-2 was detected by the assay described herein (FIG. 2). This experiment showed a sensitivity of approximately $110^{-11}$ to $110^{-10}$ M. The efficiency of detection is the slope shown in the plot in FIG. 3. The efficiency observed was probably due to the binding affinity of the antibody to which the signal oligo was attached. This antibody seems to have a Kd of approximately $1.3\times10^{-7}$. It is expected that the efficiency can be increased 100× by replacing this antibody with an antibody having a Kd of approximately $10^{-9}$.

It is expected that with improvements in efficiency and modest improvements in background, sensitivity should reach levels of $1\times10^{-13}$M but further improvements are possible with continued reduction of background This technology allows for multiplexing to levels beyond currently possible, has the potential to allow for more accurate quantification, and possibly higher sensitivity though only further development will prove the last point.

Example 2. Detection of Proteins Using Direct Measurement—Solution Triparitide—Protein Probe Attached to Reporter A diagram of the protocol for this Example is depicted in FIG. 4. In this Example the nanoreporter is attached to one of the antibodies. Preparation of the antibodies and binding to the sample happens similar to the protocol described in Example 1. In the assay described in FIG. 4 a complex of target protein and antibodies is formed in which one of the antibodies is bound to biotin and the other antibody has a nanoreporter attached.

Figure 5:
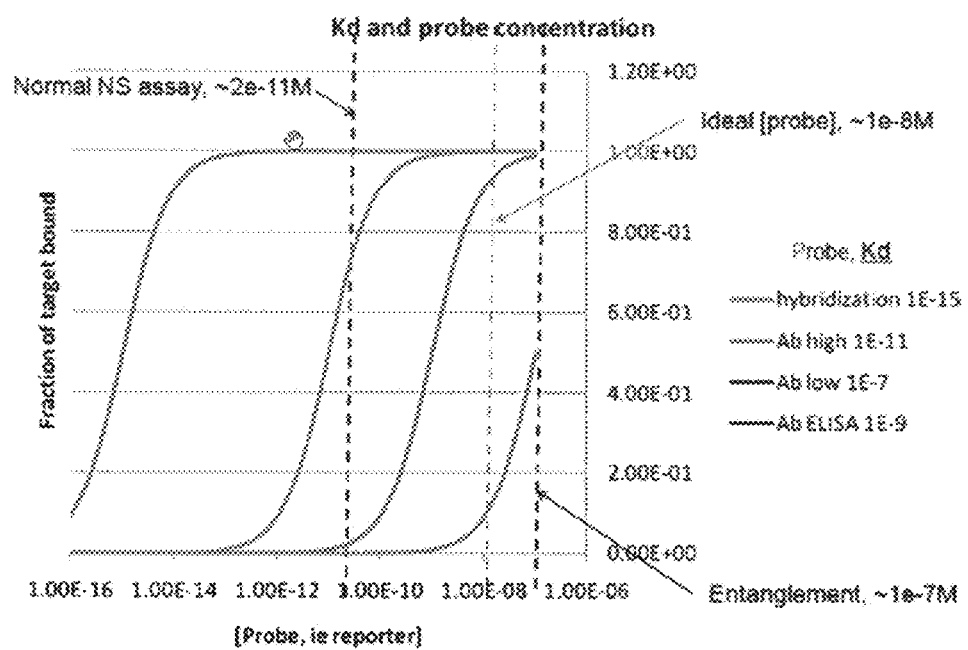
FIG. 5 is a graph depicting the dissociation constant (Kd) and probe concentration for one of the embodiments of the invention, expressed as the fraction of target bound versus the Kd of the nanoreporter probe and the protein probe.

This approach would work best with medium to low Kd antibodies, i.e., strong binding affinity. Without intending to be limited to any theory, The Kd (dissociation constant) of an antibody is usually much higher than the working concentrations of nanoreporters. In order to work with antibodies attached to nanoreporters the Kd needs to be ten times lower than the working concentration of the reporters to insure >90% binding of target to probe. FIG. 5 shows a calculation of the ideal Kd for the probes needed in this assay. FIG. 5 shows the fraction of target bound vs. the Kd of the nanoreporter probe and the protein probe. FIG. 5 shows that the ideal Kd for the protein probes would be approximately $1.0 \times 10^{-15}$ to $1.0 \times 10^{-10}$. This Kd would allow for concentrations of multiplexed reporters below the reporter entanglement threshold of $1 \times 10^{-7}$M.

Attachment of Nanoreporter to Antibody

One approach is to attach the antibody on the reporter before the binding of the antibody to the target protein. This approach requires very strong binding affinity (Kd) antibodies to allow for concentrations of multiplexed reporters significantly below the reporter entanglement threshold of $1 \times 10^{-7}$M.

A linker oligo is added to the antibody as described in Example 1. The nanoreporter is the attached to the antibody by hybridization to the linker oligo at temperatures between 37-45° C. Antibody: reporter ratio was 1:1. The labeled antibody and the reporter were hybridized at 0.05 nM, 37° C., 1×SSPE, overnight.

A second direct approach is to first bind the antibodies to the target in solution and purify the complex as described in Example 1. After the purification the nanoreporter is hybridized to the antibody (after target binding) using the protocol described above. In this approach, problems of mismatch between hybridization and protein binding are avoided.

For both these approaches, strong binding affinities are also needed to remain bound during purifications and during imaging. Basically the Koff rate (antibody dissociation from the target protein) must be longer than the time for purification and reading of the assay.

Purification of the target protein-antibodies complex can be performed as described in Example 1. Elution can be accomplished by melting off G and F beads or via digestion. However, one skilled in the art will understand that the melting off the complex might require optimization of conditions to allow for antibodies to remain bound but affinity tags to release.

The protein-antibodies complex can be bound to a coverslip coated with streptavidin (Optichem®, Accelr8 Technology Corporation), stretched and image as described in Example 1.

Stretching of a reporter hybridized to an antibody was tested to be sure that the presence of the antibody does not cause non-specific binding or stickiness to the surface that inhibited the normal binding, stretching, and imaging process (data not shown).

Example 3. Detection of Proteins Using Indirect Measurement—Sandwich Assay on a Surface A diagram of the protocol for this Example is depicted in FIG. 6. In this Example the capture antibody is attached to a surface, e.g., a magnetic bead, and the second antibody is attached to a signal oligo. The antibodies can be prepared by any methods knows in the art including the methods described in Example 1. In this example, proteins and nanoreporters are largely separate, which eliminates concerns about protein stickiness. In this assay the local antibody concentrations on the surface can be high.

The target proteins are mixed with the capture antibody on the magnetic beads (2 hours to overnight, 1×PBS, and room temperature). The unbound protein sample is washed away. The labeled antibody signal oligo complex is added to the beads with blockers (1×PBS and room temperature). After a period of binding the excess labeled antibody signal oligo complex is washed away. The isolated target protein/antibody complex is then washed and the signal oligo is eluted and analyzed as described in Example 1.

Example 6. Detection of Proteins Using Indirect Measurement—Biotinylated Signal Oligos A diagram of the protocol for this Example is depicted in FIGS. 7A and 7B. In this Example the capture antibody is attached to a surface, e.g., a magnetic bead, and the second antibody is in solution or attached to a biotinylated signal oligo. This assay provides the advantages that it requires only two bead purifications. In addition, in this assay, like in Example 2, proteins and nanoreporters are largely separate, which eliminates concerns about protein stickiness. The target proteins are mixed with the capture antibody, labeled antibody signal oligo complex, and blockers as described in Example 3. The complex of target protein and antibodies are purified using the magnetic bead in the capture antibody as described in Example 3.

The isolated target protein/antibody complex is then washed and the signal oligo is eluted as described in Example 1. The signal oligo can then be purified using Streptavidin-coupled Dynabeads® (Invitrogen) according to manufacturer's protocol. The signal oligo is then analyzed as described in Example 1.

Example 7. Detection of Proteins Using Proximity Ligation—Indirect Measurement

A diagram of the protocol for this Example is depicted in FIGS. 8A to 8D. In this assay two physically close oligos are ligated. Probes containing the oligos are designed to bind pairwise to target proteins and to form a signal oligo by ligation when the probes are brought in proximity.

This approach has several benefits around sensitivity, minimization of cross-reactivity, and multiplexing. Proximity ligations have shown high sensitivity and have the effect of lowering the apparent Kd by essentially decreasing the off-rate.

The probes containing the oligos are prepared and purified as described in Gullberg et al, PNAS 101(22), p 8420-24 (2004). The target proteins are then mixed with the probes containing the oligos and the bridging oligos by incubating samples for one hour. The components required for probe ligation are then added as described in Gullberg et al. After five minutes ligation at room temperature the signal oligo is then released as via disulfide reduction, uracil excision, restriction digest, proteinase K, or any other suitable method known in the art. Additionally, the signal oligo can be released by the methods depicted in FIGS. 8B to 8D The signal oligo is the analyzed as described in Example 1.

Alternatively, the assay can be performed as depicted in FIG. 9. In this approach, one of the oligos is attached to a nanoreporter.

This approach takes advantage of the decrease in the Koff via proximity ligation. A lower Koff means a lower Kd and the ability to work with lower concentrations of protein probe. This decrease in Kd makes it easier to work in concentrations required for reporters, and thus to contemplate direct detection approaches for multiplex analysis and lower reagent costs. This approach does not need a step for hybridization to reporters within the assay as some of the other methods proposed herein. Thus, it will be faster and have a shorter time to answer.

Using the approach described in FIG. 8C, purification conditions are optimized to eliminate ligated oligos from non-ligated oligos after release from the antibodies. For example, this purification step can be performed using magnetic beads. Importantly, if the amount of antibody used is higher than the amount of reporters used, then the resultant excess of unligated oligos may block the hybridization of the reporter to the oligo.

Antibody pairs were labeled with oligos using the methods described in Example 8. These oligos were designed to include a bridging oligo having an overlap of 9 bases and melting temperatures of 37° C. in 1×PBS. The bridging oligo had 18 bases and a biotin tag for purification purposes. The ligated oligos have 18 bases of overlap with the biotinylated bridge and, thus, the ligated oligos are more stable than the unligated oligos that are bound to the antibodies. The biotinlyated oligos are isolated from the solution on magnetic beads coated with streptavidin. It was determined that only ligated oligos have sufficiently high melting temperatures to remain attached to the biotinylated oligos following a rinsing step using stringent buffer conditions.

FIG. 13 demonstrates how various components are purified in a variety of buffer conditions. Components were present in solution at the concentrations used in the assay. The solutions were digested by protease prior to purification to release the oligos from the antibodies, as performed in the assay. As expected by melting temperature estimates, 0.03× SSPE provided the most efficient buffer. PROX05 represents a ligated product that is retained following this rinsing step.

Example 8. Detection of Proteins Using Indirect Measurements—Multiplexed Assay in Solution This example is similar to Example 1, however, the detection is multiplexed and utilizes a different coupling chemistry between the antibodies and oligos.

Bioinformatics

Signal oligos were designed with minimal cross-reactivity at a range of temperatures, typically from about 4 to about 37° C., and 1×PBS. Unique overlaps between signal oligos and labeling oligos had melting temperatures of 51 to 56 in 1×PBS to allow for hybridizing the signal oligo to the labeling oligo at 37 C. These overlaps of 15 to 17 bases had melting temperatures of 41 to 45° C. in 0.1×SSPE to allow for elution after a magnetic bead purification.

Coupling of Oligo to Antibodies

Oligos were coupled to antibodies using aldehyde-hydrazine chemistry. All antibodies and target were purchased from R&D systems, Inc. (Minneapolis, Minn.). Each antibody A (see, Table 1) was desalted using a size exclusion spin column (0.5 ml Zeba Spin Column, Fisher Scientific, Pittsburgh, Pa.). Succinimidyl 6-hydrazinonicotinate acetone hydrazone (Solulink, San Diego, Calif.) was reacted to each antibody A. Each antibody was again purified using a size exclusion spin column.

TABLE 1

Antibodies

| | | Part numbers | |
|---|---|---|---|
| Protein | Target | Antibody A | Antibody B |
| TNF alpha | 210-TA-010 | MAB610 | BAF210 |
| IL1 alpha | 200-LA-002 | MAB200 | BAF200 |
| IL6 alpha | 206-TA-010 | MAB206 | BAF206 |
| VEGF | 293-VE-010 | MAB293 | BAF293 |

The amine oligos were desalted using a membrane spin column (5K MWCO VivaSpin, Fisher Scientific, Pittsburgh, Pa.). Twenty molar equivalents succinimidyl-4-formyl benzoate (Solulink, San Diego, Calif.) were reacted with each oligo. The oligos were again purified using membrane spin columns.

Each corresponding modified oligo was reacted with the corresponding modified antibody at a molar ration of 3 to 1. This was purified on a spin column (2 ml Zeba Spin Column, Fisher Scientific, Pittsburgh, Pa.). Table 2 shows that between 1-2 oligos were attached to each antibody at the end of the counting process (Oligo:Ab).

TABLE 2

Molar substitution ratios showing quality control and quantification capabilities of antibody - oligo coupling process.

| Antibody | MSR (molar substitution ratio) | | |
|---|---|---|---|
| Protein target | 4FB:oligo | HyNic:Ab | Oligo:Ab |
| TNFalpha | 1.46 | 7.3 | 1.48 |
| IL1alpha | 2.31 | 11 | 1.53 |
| VEGF | 3.58 | 7.0 | 2.07 |
| IL6 | 1.34 | 7.4 | 1.37 |

Hybridization of Signal Oligo to Detection Antibody

Each unique signal oligo was preannealed separately to the unique oligo linked to each antibody A by adding oligo linked antibody A and corresponding signal oligo in a ratio of 4:1, signal oligo:Antibody ratio. Other ratios are contemplated.

Formation of Target and Antibodies Complex

A 2× master mix was created containing: each antibody A annealed to signal oligo and biotinylated antibody B (4 pairs) in a single tube at approximately $1\times10^{-15}$ to $1\times10^{-8}$ M, with blockers (salmon sperm). The target proteins were added to the desired dilution ($<1\times10^{-8}$M) to aliquots of this master mix. Antibodies were at 10× concentration over an estimated Kd of $10^{-15}$ to $10^{-8}$ M. The mixture was incubated.

The complex of target protein and antibodies was purified using Streptavidin-coupled Dynabeads® (Invitrogen) according to protocol.

Elution of Signal Oligo

The isolated target protein/antibody complex was washed and the signal oligo was eluted at greater than 45° C. using 0.1×SSPE for 10 to 15 minutes. Shorter and longer periods are contemplated Detection of Signal Oligo:

Detection of the signal oligo in each sample was carried out using a dual nanoreporter system having both labeled nanoreporter probes and unlabeled nanoreporter probes. The signal oligos from each sample were hybridized with final concentrations of the hybridization reagents as follows: unlabeled, biotinylated probe labeled reporter probe, 5×SSPE (pH 7.5), 5×Denhardt's reagent (Sigma), sheared salmon sperm DNA (Sigma), and detergent. Reagents were mixed and incubated in a thermocycler block with a heated lid for 16 hours.

Post-Hybridization Purification

To remove unhybridized reporters, reactions were purified over magnetic beads (Invitrogen™) coupled to oligonucleotides complementary to the 3'-repeat sequence contained on every biotinylated probe. Reactions were first diluted SSPE in 0.1% detergent mixture/TE and allowed to bind to beads at greater than 20 C with continuous rotation. The beads were washed three times in SSPE and detergent and the hybridized complexes eluted in of 0.1×SSPE/0.1%/detergent mixture for 15 minutes at 45° C. After elution, samples were purified a second time to remove excess biotinylated probes by binding to magnetic beads coupled to oligonucleotides complementary to the 5'-repeat sequence contained on every reporter probe. The elutions from the anti-3'-repeat beads were brought to a final concentration of 1×SSPE and bound for 15 minutes at 22.5° C. with rotation. Beads were washed as above and eluted in of 0.1×SSPE/0.1%/detergent mixture at greater than 40° C. The doubly-purified samples were then prepared for capture as described below.

NanoString Reporter Capture, Stretching, and Imaging

A solution of a custom-formulation of Tetraspeck fluorescent microspheres (Invitrogen™) was added to each sample. Samples were loaded into a NanoString fluidic device processed and imaged.

Results

Figure 10:
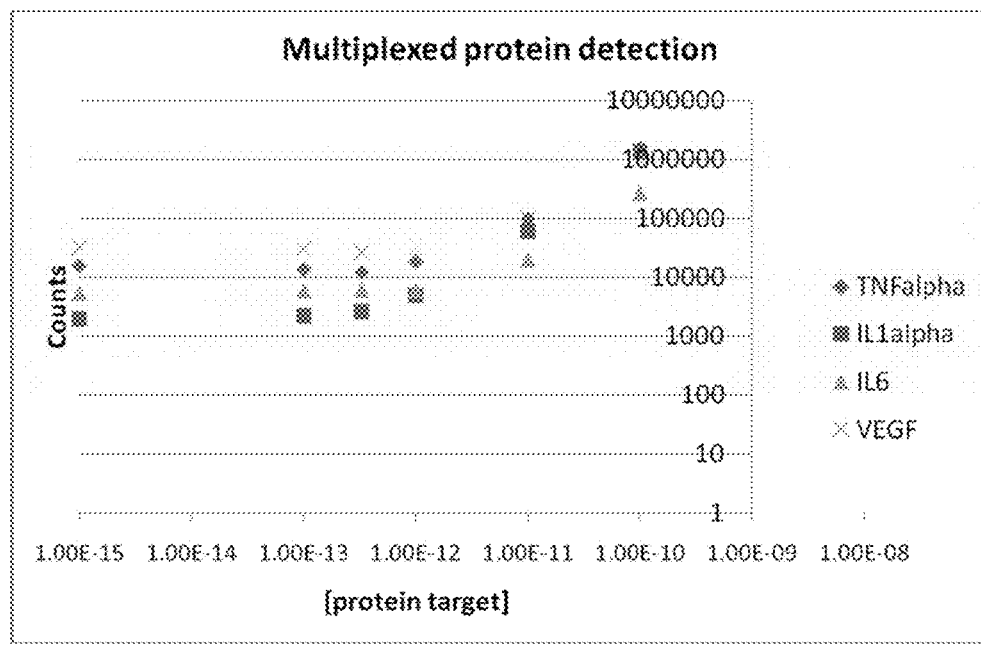
FIG. 10 is a graph depicting the results of multiplexed protein detection of TNFalpha, IL1alpha, IL6, and VEGF, measured as total counts detected as a function of increasing protein target concentration ([protein target]). In this example, a sandwich detection assay was used in solution. A 4-plex measurement is shown.
Figure 11:
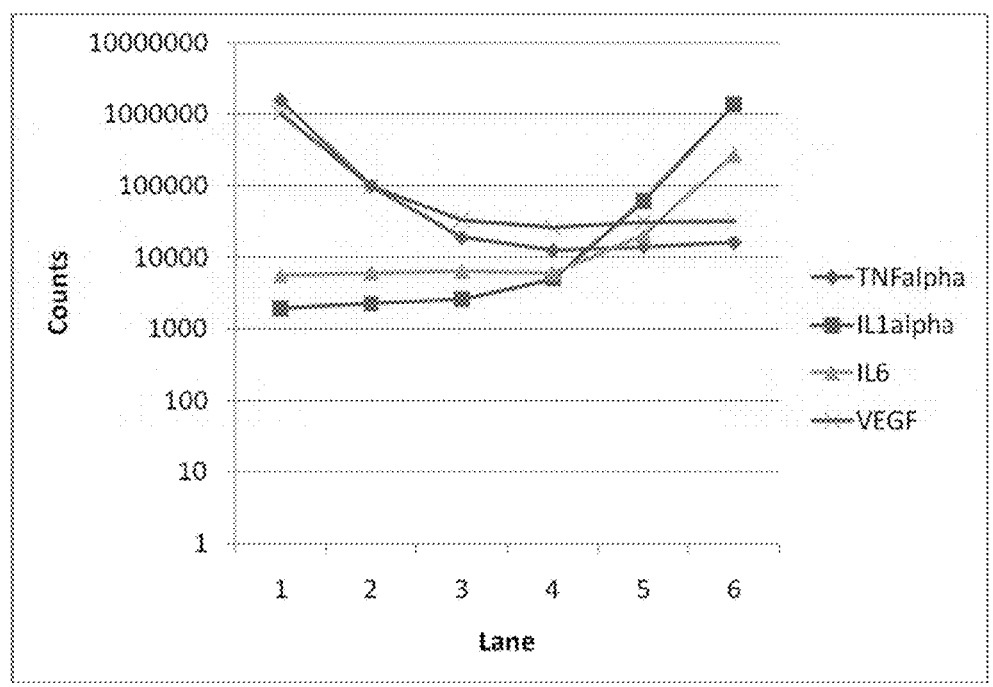
FIG. 11 is a graph depicting the data analyzed in FIG. 10, plotted by lane instead of by concentration. Specifically, this figure demonstrates that two target proteins were titrated in whereas two other protein targets were titrated out.
Figure 12:
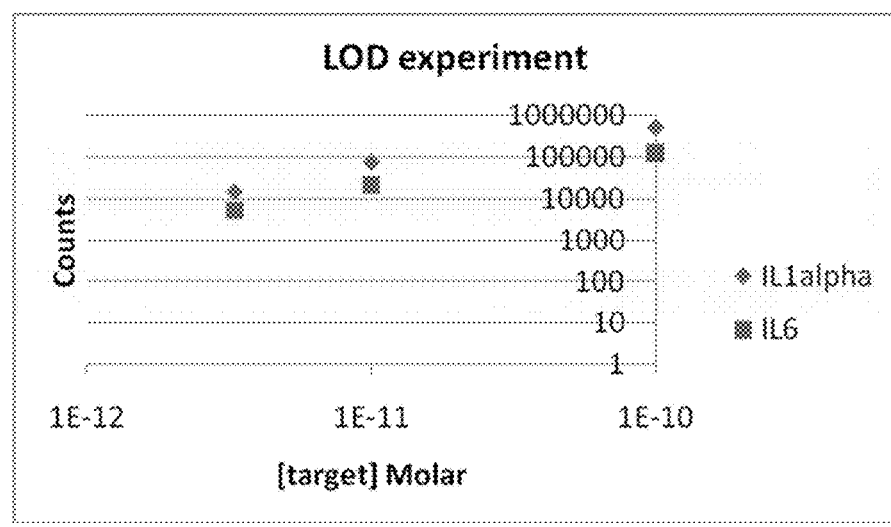
FIG. 12 is a graph depicting the results of a limit of detection (LOD) experiment using two protein targets, IL1alpha and IL6. Total counts detected were plotted as a function of increasing molar concentration of the target protein ([target] molar). The experiment demonstrated that the limits of detection were 26 and 38 picograms per milliliter (pg/ml), corresponding to $1.4 \times 10^{-12}$M and $1.9 \times 10^{-12}$M for IL1alpha (IL1$\alpha$) and IL6, respectively. The limit of detection was two standard deviations above background detection levels. Six negative controls were performed, resulting in average counts of plus or minus one standard deviation, i.e., 3196±265 and 6703±585, respectively.

Results are shown in FIG. 10. The results of this experiment showed that 4 proteins were simultaneously detected by the assay described herein (FIG. 10). The proteins detected were TNFα, IL1α, IL6, and VEGF. This experiment showed sensitivities of about $1 \times 10^{-12}$ M. FIG. 11 shows the same data plotted versus fluid sample. A subsequent experiment (FIG. 12) showed the limit of detection of two of these proteins was 26 and 38 pg/ml ($1.4 \times 10^{-12}$ and $1.9 \times 10^{-12}$ M for IL1α and IL6, respectively).

Improvements in background, i.e., reduction of background detection or the improvement of background to target detection ratios, allow for increases in sensitivities of approximately 2 orders of magnitude, thus sensitivity would reach $1 \times 10^{-14}$ M or significantly <1 pg/ml.

Example 9. Anti-Streptavidin Probe Reporter

An anti-streptavidin antibody (Affinity Bioreagents, Rockford, Ill.) was labeled with an oligonucleotide (oligo), as described in Example 1.

In a particular example of this embodiment, an antibody-labeled oligo was hybridized to a reporter at concentration of 0.05 nM, at a temperature of 45° C., in 1×SSPE buffer, overnight. There was a 25-base overlap between the reporter and oligo that was bound to the antibody. This overlap may be shortened, if desired. In certain embodiments, the overlap is optionally 1, 5, 10, 15, 20, 25 bases or any length in between. A shorter overlap of bases between the reporter and oligo on the antibody allows for increased efficiency of hybridization of the antibody-oligo to the reporter at temperatures that produce antibody stability. A reporter with an anti-streptavidin antibody probe was introduced into the flow chamber of the cartridge (at a concentration of 0.025 nM in 0.25×SSPE buffer) and a first end of the reporter was allowed to bind to the streptavidin surface for 10 minutes. The chamber was then washed with TAE buffer. The reporters were stretched and subsequently immobilized on the surface by first using an electric field of 200 volts (V)/centimeter (cm) and, second, introducing biotinlyated oligos to attach a second end of the reporter to the surface. The sample was washed again with TAE, and SlowFade™ was introduced to stabilize the dyes. This sample was then imaged.

Figure 14:
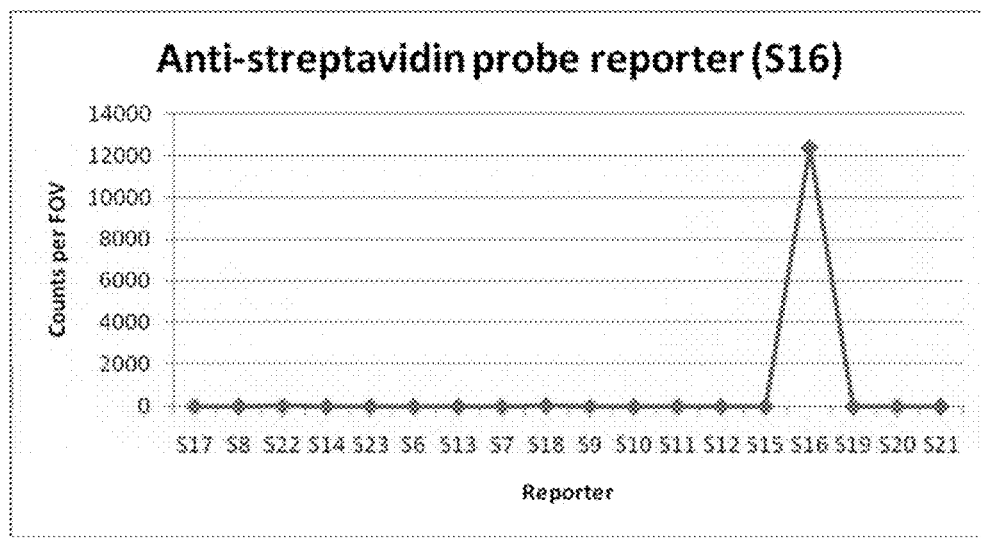
FIG. 14 is a graph showing the counts per field of view (FOV) for each antibody probe on a reporter that bound, stretched, and immobilized (S17, S8, S22, S14, S23, S6, S13, S7, S18, S9, S10, S11, S12, S15, S16, S19, S20, and S21). Counts are shown only of the reporter with the antibody probe that is bound to the surface.

FIG. 14 shows that only the reporter with the anti-streptavidin probe (S16) was detected.

OTHER EMBODIMENTS

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining the concentration of a plurality of target proteins by a method comprising
   (1) providing
      (i) a plurality of target proteins and
      (ii) a plurality of first protein-binding probes
         wherein each first protein-binding probe is attached to a single-stranded signal oligo via a linker oligo;
   (2) forming a plurality of first complexes, each first complex comprising:
      (i) at least one of said plurality of target proteins, and
      (ii) a first protein-binding probe specific for a first region of said at least one of said plurality of target proteins;
   (3) cleaving said linker oligo, thereby releasing a plurality of single-stranded signal oligos from said plurality of first complexes;
   (4) forming a plurality of second complexes, each second complex comprising:
      (i) at least one of said plurality of single-stranded signal oligos and
      (ii) an oligo probe comprising a region specific to said at least one of said plurality of single-stranded signal oligos and a region comprising a nanoreporter, wherein said nanoreporter comprises a plurality of detectable labels; and
   (5) detecting each second complex or at least part of each second complex in said plurality second complexes by a method comprising individually identifying and counting each detectable label for each of said nanoreporter,
   wherein the count of each detectable label is indicative of the concentration of one of said plurality of target proteins in said sample.

2. The method of claim 1 wherein each first protein-binding probe is independently selected from the group consisting of an antibody, a peptide, an aptamer, and a peptoid.

3. The method of claim 1 wherein the concentration of two or more target proteins is determined.

4. The method of claim 1 wherein the concentration of 2, 3, 4, 5, 10, 20, 30, 50, 100, 200, 300, 500, 600, 700, 800, 900, 1000, or more than 1000 different target proteins is determined.

5. The method of claim 1 wherein the concentration up to 2000 different target proteins is determined.

6. The method of claim 1 wherein the concentration up to 980 different target proteins is determined.

7. The method of claim 1 wherein each of said nanoreporter comprises a single-stranded nucleic acid backbone, said backbone comprising a plurality of label attachment regions covalently attached together in a linear combination, wherein each label attachment region is hybridized to a complementary polynucleotide sequence having attached thereto at least one of said plurality of detectable labels.

8. The method of claim 1 further comprising providing a plurality of second protein-binding probes, each specific for a second region of said at least one of said plurality of target proteins,
wherein each of said plurality of second protein-binding probes is attached to a second capture region or to a second matrix.

9. The method of claim 8 wherein each of said plurality of second protein-binding probes is independently selected from the group consisting of an antibody, a peptide, an aptamer, and a peptoid.

10. The method of claim 8 wherein at least one of said plurality of first complexes further comprises at least one of said second protein-binding probes.

11. The method of claim 1 wherein each of said single-stranded signal oligos is attached to a first capture region on its respective first protein-binding probe.

12. The method of claim 11 wherein said releasing of each of said single-stranded signal oligos further comprises capturing directly or indirectly said single-stranded signal oligos to a first moiety in a first matrix.

13. The method of claim 12 wherein first matrix is selected from the group consisting of a bead and an array.

14. The method of claim 1 wherein said nanoreporter further comprises a constant region, wherein said constant region comprises a plurality of repeat nucleotide sequences.

15. The method of claim 14 further comprising binding said constant region to a second moiety in said first matrix, wherein said second moiety is capable of binding said constant region.

16. The method of claim 1 wherein said nanoreporter comprises a single-stranded nucleic acid backbone, said backbone comprising a plurality of label attachment regions covalently attached together in a linear combination, wherein each label attachment region is hybridized to a complementary polynucleotide sequence having attached thereto at least one of said plurality of detectable labels.

17. The method of claim 1 wherein said detecting further comprises detecting a digital signal.

* * * * *